United States Patent
Li et al.

(10) Patent No.: US 11,969,451 B2
(45) Date of Patent: Apr. 30, 2024

(54) COMPOSITIONS AND METHODS FOR TREATING THE EYE

(71) Applicant: Johnson & Johnson Surgical Vision, Inc., Irvine, CA (US)

(72) Inventors: Wen-Hwa Ting Li, Cranbury, NJ (US); Khalid Mahmood, Lawrenceville, NJ (US); Ramine Parsa, Lawrenceville, NJ (US); Manpreet Randhawa, Robbinsville, NJ (US); Mingqi Bai, Jacksonville, FL (US); Kenneth T. Holeva, Ponte Vedra Beach, FL (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 299 days.

(21) Appl. No.: 17/099,185

(22) Filed: Nov. 16, 2020

(65) Prior Publication Data

US 2021/0145909 A1  May 20, 2021

Related U.S. Application Data

(60) Provisional application No. 62/937,458, filed on Nov. 19, 2019.

(51) Int. Cl.
| | | |
|---|---|---|
| *A61K 36/064* | (2006.01) |
| *A61K 9/08* | (2006.01) |
| *A61K 9/107* | (2006.01) |
| *A61K 31/728* | (2006.01) |
| *A61K 47/02* | (2006.01) |
| *A61K 47/10* | (2017.01) |
| *A61K 47/12* | (2006.01) |
| *A61K 47/26* | (2006.01) |
| *A61K 47/34* | (2017.01) |
| *A61K 47/38* | (2006.01) |
| *A61K 47/46* | (2006.01) |
| *A61P 27/04* | (2006.01) |

(52) U.S. Cl.
CPC .............. *A61K 36/064* (2013.01); *A61K 9/08* (2013.01); *A61K 9/1075* (2013.01); *A61K 31/728* (2013.01); *A61K 47/02* (2013.01); *A61K 47/10* (2013.01); *A61K 47/12* (2013.01); *A61K 47/26* (2013.01); *A61K 47/34* (2013.01); *A61K 47/38* (2013.01); *A61K 47/46* (2013.01); *A61P 27/04* (2018.01)

(58) Field of Classification Search
None
See application file for complete search history.

(56) References Cited

U.S. PATENT DOCUMENTS

| | | |
|---|---|---|
| 4,051,234 A | 9/1977 | Gieske et al. |
| 4,691,820 A | 9/1987 | Martinez |
| 4,992,264 A | 2/1991 | Diot et al. |
| 4,994,262 A | 2/1991 | Charbonneau et al. |
| 5,190,747 A | 3/1993 | Sekiguchi et al. |
| 5,328,682 A | 7/1994 | Pullen et al. |
| 5,467,868 A | 11/1995 | Abrams et al. |
| 5,488,815 A | 2/1996 | Abrams et al. |
| 5,577,367 A | 11/1996 | Abrams et al. |
| 5,696,686 A | 12/1997 | Sanka et al. |
| 5,704,468 A | 1/1998 | Lust et al. |
| 5,823,327 A | 10/1998 | Wu et al. |
| 6,018,931 A | 2/2000 | Byram et al. |
| 6,050,398 A | 4/2000 | Wilde et al. |
| 6,121,315 A | 9/2000 | Nair et al. |
| D435,966 S | 1/2001 | Duis et al. |
| 6,416,745 B1 | 7/2002 | Markowitz et al. |
| 6,620,420 B2 | 9/2003 | Lanzendörfer et al. |
| 6,682,722 B2 | 1/2004 | Majeti et al. |
| 7,084,104 B2 | 8/2006 | Martin et al. |
| 7,087,650 B2 | 8/2006 | Lennon |
| 7,192,615 B2 | 3/2007 | Liu et al. |
| 7,417,020 B2 | 8/2008 | Fevola et al. |
| 7,419,688 B2 | 9/2008 | Perrier et al. |
| RE41,339 E | 5/2010 | Yu et al. |
| 8,158,111 B2 | 4/2012 | Roberto et al. |
| 8,378,090 B2 | 2/2013 | Petiard et al. |
| 8,496,976 B2 | 7/2013 | Gore et al. |
| 8,628,783 B2 | 1/2014 | Lino et al. |
| 8,652,532 B2 | 2/2014 | Courtois et al. |
| 8,828,412 B2 | 9/2014 | Yu et al. |
| 9,480,645 B2 | 11/2016 | Yu |
| 10,434,050 B2 | 10/2019 | Gambogi et al. |
| 2003/0165545 A1 | 9/2003 | Huth et al. |

(Continued)

FOREIGN PATENT DOCUMENTS

| | | |
|---|---|---|
| CN | 1883469 A | 12/2006 |
| CN | 102994500 A | 3/2013 |

(Continued)

OTHER PUBLICATIONS

CN104013955A (English translation provided by Espacenet). (Year: 2014).*
Kohler, A., et al., High-Throughput Biochemical Fingerprinting of *Saccharomyces cerevisiae* by Fourier Transform Infrared Spectroscopy; PLOS/One; 2015, 10(2): 1-22; e0118052.
Kuroshima T., et al., Serological relationships among some *Pichia* species; Jpn J. Microbiol., 1976, 20(6):485-92.

(Continued)

*Primary Examiner* — Michael Barker

(74) *Attorney, Agent, or Firm* — Johnson & Johnson Surgical Vision, Inc.

(57) ABSTRACT

The present invention relates to compositions comprising one or more compounds and/or extracts which induce, promote and/or improve production/release/delivery/excretion of hyaluronic acid and/or mucin from and/or in the cornea, and methods of using the compositions to treat the eye.

13 Claims, 5 Drawing Sheets

(56) References Cited

U.S. PATENT DOCUMENTS

| | | | |
|---|---|---|---|
| 2005/0226834 | A1 | 10/2005 | Lambino et al. |
| 2006/0013778 | A1 | 1/2006 | Hodosh |
| 2006/0141014 | A1 | 6/2006 | Eknoian et al. |
| 2007/0092469 | A1 | 4/2007 | Jacobs |
| 2007/0141018 | A1 | 6/2007 | Courtois et al. |
| 2007/0196523 | A1 | 8/2007 | Koganov |
| 2009/0241242 | A1 | 10/2009 | Beatty et al. |
| 2013/0237496 | A1 | 9/2013 | Paufique |
| 2014/0186318 | A1 | 7/2014 | Ghannoum et al. |
| 2015/0305348 | A1 | 10/2015 | Andersch et al. |
| 2017/0172913 | A1 | 6/2017 | Ballesteros |
| 2018/0036225 | A1 | 2/2018 | Figueroa et al. |
| 2018/0036233 | A1 | 2/2018 | Shabaik et al. |
| 2018/0161267 | A1 | 6/2018 | Randhawa |
| 2019/0008910 | A1 | 1/2019 | Liu-Walsh et al. |

FOREIGN PATENT DOCUMENTS

| | | |
|---|---|---|
| CN | 104857526 A | 8/2015 |
| CN | 106619976 A | 5/2017 |
| CN | 106692029 A | 5/2017 |
| CN | 106890114 A | 6/2017 |
| CN | 108697635 A | 10/2018 |
| DE | 102009045753 A | 4/2011 |
| EP | 1639994 A2 | 3/2006 |
| EP | 1962875 | 5/2007 |
| EP | 2277502 | 1/2011 |
| EP | 1707191 | 6/2013 |
| EP | 2662072 | 11/2013 |
| EP | 3165257 A | 5/2017 |
| EP | 3181142 A1 | 6/2017 |
| FR | 2626469 | 8/1989 |
| FR | 2897266 A1 | 8/2007 |
| FR | 2906719 | 4/2008 |
| FR | 2938768 A1 | 5/2010 |
| FR | 2976490 | 7/2013 |
| FR | 3016521 A | 7/2015 |
| JP | A-62-212317 | 9/1987 |
| JP | S62 234011 A | 10/1987 |
| JP | 2001181160 A | 7/2001 |
| JP | 2017095377 A | 6/2017 |
| RU | 2292887 C2 | 2/2007 |
| WO | WO 02/102399 A2 | 12/2002 |
| WO | WO 2007/053271 | 5/2007 |
| WO | WO 2009/139464 A1 | 11/2009 |
| WO | WO 2010/005123 A1 | 1/2010 |
| WO | WO 2012/175868 | 12/2012 |
| WO | WO 2013/178965 A | 12/2013 |
| WO | WO 2019/123417 | 6/2019 |
| WO | WO 2020/021481 A1 | 1/2020 |

OTHER PUBLICATIONS

Gurram (Role of Components in the Formation of Self-Microemulsifying Drug Delivery Systems, Indian Journal of Pharmaceutical Sciences., 77(3), 249-257; Year: 2015.
Passoth (Biotechnology, physiology, and genetics of the yeast *Pichia anomala*, Dept. Micro, Uppsala Genetic Centr., SLU, a6, Sep. 2005: Year 2005.
Li (Molecular Modification of Polysaccharides and Resulting Bioactives, Food Science and Food Safety, IFT, vol. 15, Year: 2016.
Pranab K. Mukherjee, et al., "Oral Mycobiome Analysis of HIV-Infected Patients: Identification of Pichia as an Antagonist of Opportunistic Fungi," Plos Pathogens, vol. 10, No. 3, Mar. 13, 2014 e1003996, XP055543219, DOI: 10.1371/journal.ppat.1003996—whole document.
Sundaramoorthy Balaabirami, et al., "Screening of new yeast *Pichia manchurica* for arabitol production", Journal of Basic Microbiology, Germany, vol. 59, No. 3, Feb. 28, 2019, pp. 256-266, XP009524256. Extended Search Report—Appln. No. 20187518.4-1112—dated Sep. 12, 2020.
European Search Report dated Dec. 19, 2017, for EP Application No. 19194767.0.
European Search Report dated Dec. 19, 2017, for EP Application No. 19194766.2.0.
European Search Report dated Dec. 19, 2017, for EP Application No. 19194773.8.
Mintel Database GNPD [Online], "Face Lift SPF 20" Sep. 2011 (XP055648134.
Li Wen-Hwa et al: "Topical stabilized retinol treatment induces the expression of HAS genes and HA production in human skin in vitro and in vivo", Archives of Dermatological Research, Springer, International, Berlin, DE (2017).
Ando et al., Int. J. Mol. Sci., 11, pp. 2566-2575, (2006).
deGuertechin, L. Oldenhhove, "Classification of Surfactants", Handbook of Cosmetic Science and Technology, eds. A. Barel, M. Paye and H. Maibach and published by Marcel Dekker, Inc. New York, NY, Chapter 37, pp. 431-450, (2001).
Handbook of Non-Invasive Methods and the Skin, eds. J. Serup, G. Jemec & G. Grove, Chapter 66.1 (2006).
Henry, N. et al., "Synthesis of a molecularly imprinted polymer to isolate glucosamine from plant extracts by an ionic-non-covalent dual approach", International Journal of Cosmetic Science, 2015, 37, 196-206.
Sirtuin Support Facial Contour Lifting Serum, Skinn Cosmetics, Sep. 2010.
Solano et al., Pigment Cell Res. 19, pp. 550-571, (2006).
UGL Complex, Barnet Products Corporation, Apr. 8, 2010.
Zocchi, G., Skin Feel Agents, Handbook of Cosmetic Science and Technology, eds. A. Barel, M. Paye and H. Maibach and published by Marcel Dekker, Inc. New York, NY, Chapter 35, pp. 399-415, (2001).
Anonymous, "Olivem 1000", Nov. 2, 2002, retrieved from the internet, URL:https://www.lotioncrafter.com/reference/Olivem_1000.pdf [retrieved on Feb. 6, 2011] (XP055448618).
Baviera et al., "Microbiota in Healthy Skin and in Atopic Eczema", BioMed Research International (2014), vol. 2014, pp. 1-6, DOI 10.1155/2014/436921.
Mintel Database GNPD [Online], "Anti-aging neck cream", Nov. 2011 (XP002777989).
Mintel Database GNPD [Online], "Gel cream", Nov. 2015 (XP002777990).
Mintel Database GNPD [Online], "Twinkle Twinkle facial lotion", Feb. 2013 (XP002777991).
Miyazaki et al., "Genistein and daidzein stimulate hyaluronic acid production in transformed human keratinocyte culture and hairless mouse skin", Skin Pharmacology and Applied Skin Physiology (2002) 15(3):175-183.
Sharpell and Manowitz, Chapter 51 "Preservation of Cosmetics", pp. 887-900, Disinfection, Sterilization, and Preservation, Fourth Edition, ed. Seymour S. Block, Part VII Antimicrobial Preservatives and Protectants, published by Lea & Febiger, Philadelphia, PA (1991).
Luciano Polonellirodolfo Lorenziniflavia De Bernardsigiulia Morace: "Potential therapeutic effect of yeast killer toxin", Mycopathologia, Kluwer Academic Publishers, XX, vol. 96, No. 2, (Nov. 1, 1986), pp. 103-107, XP009193593.
Street R.A. et al.: "Cichorium intybus: Traditional uses, phytochemistry, pharmacology, and toxicology", Evidence-Based Complementary and Alternative Medicine 2013 Oxford University Press GBR, vol. 2013, 2013, XP55160986.
European Search Report for EP Application No. 16205177 dated Mar. 6, 2017.
O'Goshi, "Suction Chamber Method for Measurement of Skin Mechanics: The Cutometer", Handbook of Non-Invasive Methods and the Skin, 2nd Edition, eds. J. Serup, G. Jemec & G. Grove, Chapter 66 (2006) pp. 579-582.
European search report dated Feb. 20, 2018, for EP application 17206433.9.
Frenkel ES, Ribbeck K, "Salivary mucins in host defense and disease prevention," J Oral Microbiol., 2015; 7: 29759.
Kashyap B, Kullaa AM., Regulation of mucin 1 expression and its relationship with oral diseases, Archives of Oral Biology, 117: 104791; 2020.

(56) References Cited

OTHER PUBLICATIONS

Chang, W.I., Chang, J.Y., Kim, Y.Y., Leeb, G., & Kho, H.S. MUC1 expression in the oral mucosal epithelial cells of the elderly, Archives of Oral Biology, 2011; 56, 885-890.
Sengupta A., Valdramidou, D., Huntly, S., Distribution of MUC1 in the normal human oral cavity is localized to the ducts of minor salivary glands, Arch Oral Biol., 2001; 46: 529-38.
Pramanik, R., Osailan, S.M., Challacombe, S.J., et al., Protein and mucin retention on oral mucosal surfaces in dry mouth patients, Eur J Oral Sci, 2010; 118: 245-53.
Akira, S., & Takeda, K., Toll-like receptor signalling. Nature Reviews Immunology, 2004; 4(7), 449-511.
Ueno, K., Koga, T., Kato, K., Golenbock, D. T., Gendler, S. J., Kai, H., & Kim, K. C. MUC1 mucin is a negative regulator of toll-like receptor signalling. American Journal of Respiratory Cell and Molecular Biology. 2008; 38, 263-268.
*Annual review of selected scientific literature: A report of the Committee on Scientific Investigation of the American Academy of Restorative Dentistry*. Journal of Prosthetic Dentistry (Dec. 2008) pp. 816-877.
Lundmark A, Johannsen G, Eriksson K, Kats A, Jansson L, Tervahartiala T, et al. *Mucin 4 and matrix metalloproteinase 7 as novel salivary biomarkers for periodontitis*. J Clin Periodontal 2017; 44:247-54.
U.S. Appl. No. 62/724,807, filed Aug. 30, 2018, JJCI.
U.S. Appl. No. 16/266,607, filed Feb. 4, 2019, 2020-0069562, Mar. 5, 2020, JJCI (Abandoned).
U.S. Appl. No. 62/724,812, filed Aug. 30, 2018, JJCI.
U.S. Appl. No. 16/266,645, filed Feb. 4, 2019, 2020-0069564, Mar. 5, 2020, JJCI.
U.S. Appl. No. 62/724,820, filed Aug. 30, 2018, JJCI.
U.S. Appl. No. 16/266,694, filed Feb. 4, 2019, 2020-0069564, Mar. 5, 2020, JJCI.
U.S. Appl. No. 62/432,945, filed Dec. 12, 2016, JJCI.
U.S. Appl. No. 15/799,350, filed Oct. 31, 2017, 2018/0161267, Jun. 14, 2018, JJCI (Granted—U.S. Pat. No. 10,206,870).
U.S. Appl. No. 16/117,434, filed Aug. 30, 2018, 2019/0008910, Jan. 10, 2019, JJCI (Granted—U.S. Pat. No. 10,543,240).
U.S. Appl. No. 62/268,618, filed Dec. 17, 2015, JJCI.
U.S. Appl. No. 15/375,365, filed Dec. 17, 2016, 2017/0172913, Jun. 22, 2017, JJCI (Abandoned).
U.S. Appl. No. 62/703,941, filed Jul. 27, 2018, JJSVI.
U.S. Appl. No. 16/519,149, filed Jul. 23, 2019, JJSVI.
U.S. Appl. No. 62/703,948, filed Jul. 27, 2018, JJSVI.
U.S. Appl. No. 16/519,161, filed Jul. 23, 2019, JJSVI (Abandoned).
U.S. Appl. No. 17/029,236, filed Sep. 23, 2020, JJSVI.
U.S. Appl. No. 62/877,395, filed Jul. 23, 2019, JJCI.
U.S. Appl. No. 16/933,512, filed Jul. 20, 2020, JJCI.
Bowen, P.; "Particle Size Distribution Measurement from Millimeters to Nanometers and from Rods to Platelets," Journal of Dispersion Science and Technology, Taylor and Francis Group, NY; vol. 23, No. 5, Jan. 1, 2002; pp. 631-662.
Extended European Search Report, Appln. No. 20208692.2-1112, dated Mar. 16, 2021.
Bonneheure Anti-Wrinkle Nutritious Eye Cream, North China Pharmaceutical Qinhuangdao Co., Ltd., a filing platform for domestic non-special use cosmetics, website: http://ftba.nmpa.gov.cn: 8 181/ftban/itownet/hzp_ba/fw/pz.jsp?processid=20141117151746h7y9n &nid=201 41117151746h7y9nE—Jan. 6, 2015 (E-Certificate from the National Medical Products Administration (NMPA). It was only published in Chinese. (English Translation).
Cheled-Shoval S.L., et al., "Differences in Intestinal Mucin Dynamics Between Germ-free and Conventionally Reared Chickens After Mannan-oligosaccharide Supplementation," Poultry Science, Mar. 2014, vol. 93(3), pp. 636-644.
Hino S., et al., "Small Intestinal Goblet Cell Proliferation Induced by Ingestion of Soluble and Insoluble Dietary Fiber is Characterized by an Increase in Sialylated Mucins in Rats," The Journal of Nutrition, Aug. 2012, vol. 142(8), pp. 1429-1436.
Japanese Pharmacopoeia Sodium Hyaluronate Ophthalmic Solution., "Ophthalmic Solution, 0.1% Hyalein Mini Ophthalmic Solution, 0.1%, Hyaluronic Acid Ophthalmic Solution, 0.3% Hyalein Mini Ophthalmic Solution 0.3%," 2018, 84 pages.
Otsuka Pharmaceutical Co., Ltd., "Mucostat Eyedrop UD 2%—Rebamipide Suspension ophthalmic Solution," 2012, 8 pages.
Craig, J.P. et al. TFOS DEWS II definition and classification report. *Ocul Surf*. 2017; 15: 276-283.
Dai, et al., 2013 (Liposomes containing bile salts as novel ocular delivery systems for tacrolimus (FK506): in vitro characterization and improved corneal permeation, International Journal of Nanomedicine 2013:8 1921-1933). (Year: 2013).
David A. Leigh et al. Angew. Chem Int. Ed., 2001, 40, No. 8, pp. 1538-1542.
Douglass, et al. 2018 (Population genomics shows no distinction between pathogenic Candida krusei and environmental Pichia kudriavzevii: Once species, four names, PLOS Pathog 14(7): e 1007138; https://doi.org/10.1371/journal.ppat.1007138 (Year: 2018).
Dreyfuss JL, Regatieri CV, Coelho B, et al. Altered hyaluronic acid content in tear fluid of patients with adenoviral conjunctivitis. An Acad Bras Cienc. 2015;87(1):455-462.
Eric Carlson, et al., "Impact of Hyaluronic Acid-Containing Artificial Tear Products on Reepithelialization in an In Vivo Corneal Wound Model", Journal of Ocular Pharmacology and Therapeutics, vol. 34, No. 4, pp. 360-364, May 1, 2018.
International Search Reports dated Nov. 28, 2019 PCT/IB2019/056345 and PCT/IB2019/056341 dated Nov. 29, 2019.
Jean-Claude Chambron et al. Pure & Appl. Chem., 1990, vol. 62, No. 6, pp. 1027-1034.
Kurtzman, et al. 2008 (Phylogenetic relationships among species of *Pichia, Issatchenkia* and *Williopsis* determined from multigene sequence analysis, and the proposal of *Barnettozyma* gen.nov., *Lindnera* gen.nov. and *Wickerhamomyces* gen.nov.FEMS Yeast Res 8 (2008) 939-954) (Year: 2008).
Laemmli UK. 1970., Cleavage of structural proteins during the assembly of the head of bacteriophage T4. Nature 227: 680-685.
Maker AV, Katabi N, Gonen M, et al. Pancreatic cyst fluid and serum mucin levels predict dysplasia in intraductal papillary mucinous neoplasms of the pancreas. *Ann Surg Oncol*. 2011;18(1):199-206.
Martins Jr, Passerotti CC, Maciel RM, Sampaio Lo, Dietrich CP and Nader HB. 2003., Practical determination of hyaluronan by a new noncompetitive fluorescence-based assay on serum of normal and cirrhotic patients. Anal Biochem 319: 65-72.
Pacella, E., Pascella, F., De Paolis, G., et al. *Glycosaminoglycans in the human cornea*: age-related changes. Ophthalmol. Eye Dis. 7:1-5, 2015).
U.S. Appl. No. 60/783,557, filed Mar. 17, 2006.
Uchino Y, Uchino M, Yokoi N, et al. Alteration of Tear Mucin 5AC in Office Workers Using Visual Display Terminals: The Osaka Study. *JAMA Ophthalmol*. n2014;132(8):985-992.
U.S. Appl. No. 16/266,645, filed Feb. 4, 2019, 2020-0069563, Mar. 5, 2020, JJCI (Granted—U.S. Pat. No. 11,045,416).
U.S. Appl. No. 16/266,694, filed Feb. 4, 2019, 2020-0069564, Mar. 5, 2020, JJCI (Granted—U.S. Pat. No. 11,110,051).
U.S. Appl. No. 62/286,618, filed Dec. 17, 2015, JJCI.
U.S. Appl. No. 16/519,149, filed Jul. 23, 2019, JJSVI (Granted—U.S. Pat. No. 11,166,997).
U.S. Appl. No. 17/515,882, filed Nov. 1, 2021, JJSVI.
U.S. Appl. No. 15/519,161, filed Jul. 23, 2019, JJSVI (Abandoned).
U.S. Appl. No. 17/029,236, filed Sep. 23, 2020, JJSVI (Granted—U.S. Pat. No. 11,357,805).
U.S. Appl. No. 17/737,513, filed May 5, 2022, JJSVI.
U.S. Appl. No. 62/877,395, filed Jul. 23, 2019, JJCI (Abandoned).
U.S. Appl. No. 16/933,512, filed Jul. 20, 2020, JJSVI (Abandoned).
Wang Chengye, Causes and Treatment of Complications in Eye Surgery; Human Science and Technology Press, Jun. 1998; p. 218 (Abstract).
Gu Qisheng, Yan Kai, Hyaluronan-based Biomaterials in Clinical Medicine, Second Military Medical University Press, Nov. 2003, p. 306 (Abstract).
U.S. Appl. No. 16/266,645, filed Feb. 4, 2019, 2020-0069563, Mar. 5, 2020.
U.S. Appl. No. 16/266,694, filed Feb. 4, 2019, 2020-0069564, Mar. 5, 2020.
U.S. Appl. No. 16/933,512, filed Jul. 20, 2020.

(56) References Cited

OTHER PUBLICATIONS

U.S. Appl. No. 17/029,236, filed Sep. 23, 2020.
U.S. Appl. No. 62/286,618, filed Dec. 17, 2015.
U.S. Appl. No. 62/432,945, filed Dec. 12, 2016.
U.S. Appl. No. 62/703,948, filed Jul. 27, 2018.
U.S. Appl. No. 62/724,807, filed Aug. 30, 2018.
U.S. Appl. No. 62/724,812, filed Aug. 30, 2018.
U.S. Appl. No. 62/724,820, filed Aug. 30, 2018.
U.S. Appl. No. 62/877,395, filed Jul. 23, 2019.
U.S. Appl. No. 62/937,458, filed Nov. 19, 2019.
Co-pending U.S. Appl. No. 16/519,161, filed Jul. 23, 2019.

* cited by examiner

COMPOSITIONS AND METHODS FOR TREATING THE EYE

CROSS REFERENCE TO RELATED APPLICATION

The present application claims the benefit of the earlier filing date of U.S. provisional patent applications 62/937,458 and 62/937,473, each, filed Nov. 19, 2019, the entirety of each such application is hereby incorporated by reference herein as if fully set forth herein.

FIELD OF THE INVENTION

The present invention relates to compositions comprising one or more compounds and/or extracts which induce, promote and/or improve production/release/delivery/excretion of mucin from and/or in the cornea, and methods of using the compositions to treat the eye.

BACKGROUND OF THE INVENTION

"Dry eye is a multifactorial disease of the ocular surface characterized by a loss of homeostasis of the tear film, and accompanied by ocular symptoms, in which tear film instability and hyperosmolarity, ocular surface inflammation and damage, and neurosensory abnormalities play etiological roles." Craig, J. P. et al. TFOS DEWS II definition and classification report. *Ocul Surf* 2017; 15: 276-283. Dry eye can result from abnormal or inadequate tear formation, and deficiency in mucin secretion (i.e., keratoconjunctivitis sicca).

Dry eye symptoms can be manifest as a result of various underlying disorders such as autoimmune disorders that damage lacrimal (i.e., tear-producing) glands, such as rheumatoid arthritis, Sjögren's syndrome, systemic lupus erythrematosus, and systemic sclerosis and sarcoidosis. Dry eye can also be induced following eye surgery, such as Lasik® surgery. Dry eye is estimated to affect more than 13 million individuals in the United States.

Regardless of the underlying pathology, dry eye commonly involves the rapid breakdown of the pre-ocular tear film, resulting in dehydration of the exposed outer surface. Normal tear formation is required to keep the cornea and conjunctiva moist, and this in turn helps to prevent ulceration of both, as well as to maintain corneal transparency. In addition, tears facilitate movement of the eyelid over the eye surface (e.g., blinking) and removal of foreign substances from the eye. Tears also normally contain lysozyme which is useful in preventing infection in the eye. Dry eye can be associated with mild discomfort to severe pain in the eye. When it occurs for prolonged periods of time, it can cause blurred vision, grittiness and/or burning sensation, and itchiness. If the condition is allowed to persist without treatment, it can further lead to corneal ulcers and/or scarring.

Dry eye symptoms include eye pain or fatigue, increased blinking, and bloodshot eyes. Further, bacteria may enter through a scratch and cause infection, and if the scratch is deep enough it can even affect the vision of the person. In addition to eyestrain, causes of dry eye include Sjogren's syndrome, Stevens-Johnson syndrome, burns and injury to the eye, and side effects of hypotensive drugs, tranquilizers, eyedrops for treating glaucoma, and other such drugs.

Eyedrops are an effective way to treat dry eye. Such eyedrops typically include dry-eye treatment actives—a common active in such eyedrops is hyaluronic acid. Hyaluronic acid is a biologically derived macromolecular substance, has extremely high water retention and characteristic properties such as high viscoelasticity, good thickening property, and good thread-forming ability, and has been used as a humectant in topical agents for treating various kinds of skin problems and so forth. In the case of dry eye caused by Sjogren's syndrome, in which dryness is seen over the entire body, the application of eyedrops containing hyaluronic acid is effective. However, when instilled as an eyedrop, hyaluronic acid has a relatively short residence time on the cornea, so the effect of hyaluronic acid eyedrops lasts only about 2 or 3 hours, which means that the patient must apply the drops more frequently (such as 5 to 10 times a day).

Hyaluronic acid (HA) is produced by corneal epithelial cells in the eye. Notably, significantly higher hyaluronic acid concentrations have been found in the corneas of younger human population than in the older. (See Pacella, E., Pascella, F., De Paolis, G., et al. *Glycosaminoglycans in the human cornea: age-related changes*. Ophthalmol. Eye Dis. 7:1-5, 2015).

In addition, the tear film is the body's natural defense against dry eye. The tear film contains ocular mucins and is essential for maintaining the homeostasis of the wet ocular surface. Mucins are produced, among other places, by corneal epithelial cells in the eye. Mucins are glycoproteins expressed by epithelial tissues of mucosal surfaces. They protect tissues by functioning as antioxidants and providing lubrication. Mucin genes associated with the tear film include MUC1, MUC2, MUC4, MUC5AC, MUC5B, MUC7 and MUC16.

Mucin is also useful as an antimicrobial and both Mucin and hyaluronic acid are useful for general wound healing, and is essential for overall eye health maintenance.

There is therefore a need for an ophthalmic pharmaceutical composition that would promote and/or improve the production and/or release of hyaluronic acid and/or mucin from and/or in the cornea.

The present inventors have discovered extracts, or sources of extracts, of the genus *Pichia* which can induce, promote and/or improve production/release/delivery/excretion of hyaluronic acid and/or mucin from and/or in the cornea.

Accordingly an aspect of the present invention relates to microemulsion compositions comprising a safe and effective amount of one or more extracts, or sources of extracts, of the genus *Pichia* to induce, promote and/or improve production/release/delivery/excretion of hyaluronic acid and/or mucin from and/or in the cornea.

Another aspect of the present invention relates to methods for inducing, promoting and/or improving production/release/delivery/excretion of hyaluronic acid and/or mucin from and/or in the cornea comprising the step of administering ophthalmic microemulsion compositions comprising a safe and effective amount of one or more extracts, or sources of extracts, of the genus *Pichia*.

Another aspect of the present invention relates to methods for treating (e.g., reducing) and/or preventing dry eye, or the symptoms associated with dry eye, comprising the step of administering ophthalmic microemulsion compositions comprising one or more extracts, or sources of extracts, of the genus *Pichia*.

A further aspect of the present invention relates to methods for treating (e.g., reducing) and/or preventing dry eye, or the symptoms associated with dry eye, comprising the step of administering ophthalmic microemulsion compositions comprising one or more extracts, or sources of extracts, of the genus *Pichia*.

Another aspect of the present invention relates to methods of preventing and/or treating (e.g., reducing) eye symptoms associated with dry eye and/or resulting from decreased or low-level production/release/delivery/excretion of hyaluronic acid and/or mucin from and/or in the cornea by administering compositions comprising a safe and effective amount of one or more extracts, or sources of extracts, of the genus *Pichia*.

One aspect of the present invention relates to compositions comprising a safe and effective amount of safe and effective amount of one or more extracts, or sources of extracts, of the genus *Pichia* to induce, promote and/or improve production/release/delivery/excretion of hyaluronic acid and/or mucin from and/or in the cornea, which compositions can be administered to patients having a MUC5AC concentration in tears lower than 6 (or about 6), optionally 8 (or about 8), nanograms per milligram of proteins, such that the concentration of MUC5AC in the tears is raised to (or, is made to be) equal to or greater than 8 (or about 8) nanograms to 15 (or about 15) nanograms, optionally from 9 (or about 9) nanograms to 12 (or about 12) nanograms, per milligram of proteins.

In certain embodiments, the above-described concentration of MUC5AC in the tears (i.e., equal to or greater than 8 (or about 8) nanograms to 15 (or about 15) nanograms, optionally from 9 (or about 9) nanograms to 12 (or about 12) nanograms, per milligram of proteins), resulting from the compounds and/or extracts which induce, promote and/or improve production/release/delivery/excretion of hyaluronic acid and/or mucin from and/or in the cornea is maintained for a period of up to, at least, about 2 hours, optionally about 4 hours, optionally about 6 hours, optionally about 8 hours, optionally about 10 hours, optionally about 12 hours, or optionally from about 12 to about 24 hours.

Concentrations of MUC5AC in tears detailed above are determined using the Uchino Method (described below in the definitions).

A similar aspect of the present invention relates to methods for inducing, promoting and/or improving production/release/delivery/excretion of hyaluronic acid from and/or in the cornea comprising the step of administering ophthalmic compositions comprising safe and effective amount of one or more extracts, or sources of extracts, of the genus *Pichia* to induce, promote and/or improve production/release/delivery/excretion of hyaluronic acid and/or mucin from and/or in the cornea, which compositions can be administered to patients having a hyaluronic acid concentration, in their tears, lower than 10 (or about 10) nanograms, optionally lower than 15 (or about 15) nanograms, optionally lower than 20 (or about 20) nanograms, or optionally lower than 25 (or about 25) nanograms, per milligram of proteins, such that the concentration of hyaluronic acid in their tears is raised to (or, is made to be) equal to or greater than 10 (or about 10), optionally equal to or greater than 15 (or about 15), optionally equal to or greater than 20 (or about 20), optionally equal to or greater than 25 (or about 25) nanograms, optionally equal to or greater than 30 (or about 30), optionally equal to or greater than 35 (or about 35), optionally equal to or greater than 40 (or about 40), or optionally equal to or greater than 45 (or about 45) nanograms per milligram of proteins to 100 (or about 100), optionally 90 (or about 90), optionally 80 (or about 80), optionally 70 (or about 70), or optionally 60 (or about 60) nanograms per milligram of proteins.

In certain embodiments, the above-described concentration of hyaluronic acid, in the patients' tears, resulting from the compounds and/or extracts of the present invention is maintained for a period of up to, at least, about 2 hours, optionally about 4 hours, optionally about 6 hours, optionally about 8 hours, optionally about 10 hours, optionally about 12 hours, or optionally from about 12 to about 24 hours.

Concentrations of hyaluronic acid detailed above are determined using the Dreyfuss Method (described below in the definitions).

A further aspect of the present invention relates to methods of promoting healing or increasing the rate of healing of wounds in and/or on the eye (e.g., non-dry eye associated, eye trauma, postoperative surgical or nonspecific wounds) of a patient by administering compositions comprising a safe and effective amount of one or more extracts, or sources of extracts, of the genus *Pichia* which induce, promote and/or improve production/release/delivery/excretion of hyaluronic acid or mucin from and/or in the cornea (namely, to increase production/release/delivery/excretion of hyaluronic acid or mucin from and/or in the cornea), in certain embodiments, beyond the respective concentration levels of hyaluronic acid or mucin ordinarily produced by such patient without (or absent) administration of the compositions comprising a safe and effective amount of the one or more extracts, or sources of extracts, of the genus *Pichia*).

A still further aspect of the present invention relates to methods for improving the antimicrobial properties in tears (or, the tear film of the eye) of a patient by administering compositions comprising a safe and effective amount of one or more extracts, or sources of extracts, of the genus *Pichia* which induce, promote and/or improve production/release/delivery/excretion of hyaluronic acid and/or mucin from and/or in the cornea (namely, to increase production/release/delivery/excretion of mucin from and/or in the cornea, in certain embodiments, beyond the concentration level of mucin ordinarily produced by such patient without (or absent) the administration of the compositions comprising a safe and effective amount of such one or more extracts, or sources of extracts, of the genus *Pichia*).

SUMMARY OF THE INVENTION

The present invention relates to a microemulsion composition for treating the eye comprising:
i) one or more extracts, or sources of extracts, of the genus *Pichia*; and
ii) an ophthalmologically acceptable carrier
wherein the microemulsion droplets or particles have a maximum dimension of less than 1,500 Å.

The present invention relates to methods for producing/releasing/delivering/excreting mucin from and/or in the cornea comprising the step of administering (optionally, in a patient in need of such production/release/deliverance/excretion of mucin) a composition, in certain embodiments an ophthalmic microemulsion composition, comprising:
i) one or more extracts, or sources of extracts, of the genus *Pichia*;
ii) optionally, a safe and effective amount of a permeation enhancer; and
iii) optionally, an ophthalmologically acceptable carrier
wherein the microemulsion droplets or particles have a maximum dimension of less than 1,500 Å.

The present invention relates to methods for preventing or treating the symptoms associated with dry eye comprising the step of topically administering (optionally, in a patient need of such prevention or treatment) a microemulsion composition comprising:

i) one or more extracts, or sources of extracts, of the genus *Pichia*;
ii) one or more demulcents or soothing agents;
iii) optionally, a safe and effective amount of a permeation enhancer; and
iv) optionally, an ophthalmologically acceptable carrier wherein the microemulsion droplets or particles have a maximum dimension of less than 1,500 Å.

The present invention relates to methods for maintaining the concentration of MU5AC in tears within the range of equal to or greater than 8 nanograms to 15 nanograms per milligrams of protein, comprising the step of administering (optionally, in a patient in need of such maintenance) a microemulsion composition comprising:
i) one or more extracts, or sources of extracts, of the genus *Pichia*;
ii) optionally, a safe and effective amount of a permeation enhancer; and
iii) optionally, an ophthalmologically acceptable carrier wherein the microemulsion droplets or particles have a maximum dimension of less than 1,500 Å.

The present invention relates to methods for treating a patient having decreased or low-level production/release/delivery/excretion of mucin from and/or in the cornea comprising the step of topically administering to the eye the patient a microemulsion composition comprising:
i) one or more extracts, or sources of extracts, of the genus *Pichia*;
ii) optionally, a safe and effective amount of a permeation enhancer; and
iii) optionally, an ophthalmologically acceptable carrier wherein the microemulsion droplets or particles have a maximum dimension of less than 1,500 Å.

The present invention relates to methods for preventing or treating the symptoms associated with dry eye comprising the step of topically administering to a patient (optionally, in a patient need of such prevention microemulsion or reduction in dry eye symptoms) a microemulsion composition comprising:
i) one or more extracts, or sources of extracts, of the genus *Pichia*;
ii) optionally, a safe and effective amount of a permeation enhancer; and
iii) optionally, an ophthalmologically acceptable carrier wherein the microemulsion droplets or particles have a maximum dimension of less than 1,500 Å.

The present invention relates to methods for promoting healing or increasing the rate of healing of wounds in and/or on the eye (optionally, of a patient in need of such eye wound healing), comprising the step of administering a microemulsion compositions (i.e., which increase production/release/delivery/excretion of mucin and/or hyaluronic acid from and/or in the cornea, in certain embodiments, beyond the concentration level of mucin produced by such patient without (or absent) administration of the microemulsion compositions comprising a safe and effective amount of one or more extracts, or sources of extracts, of the genus *Pichia*) comprising:
i) one or more extracts, or sources of extracts, of the genus *Pichia*; and
ii) optionally, an ophthalmologically acceptable carrier wherein the microemulsion droplets or particles have a maximum dimension of less than 1,500 Å.

The present invention relates to methods for improving the antimicrobial properties in tears (or, the tear film of the eye) of a patent (optionally, in a patient need of such antimicrobial properties), comprising the step of administering a microemulsion compositions (i.e., which increase production/release/delivery/excretion of mucin and/or hyaluronic acid from and/or in the cornea, in certain embodiments, beyond the concentration level of mucin produced by such patient without (or absent) administration of the microemulsion compositions comprising a safe and effective amount of one or more extracts, or sources of extracts, of the genus *Pichia*) comprising:
i) one or more extracts, or sources of extracts, of the genus *Pichia*;
ii) optionally, a safe and effective amount of a permeation enhancer; and
iii) optionally, an ophthalmologically acceptable carrier wherein the microemulsion droplets or particles have a maximum dimension of less than 1,500 Å.

DETAILED DESCRIPTION OF INVENTION

Figure 1:
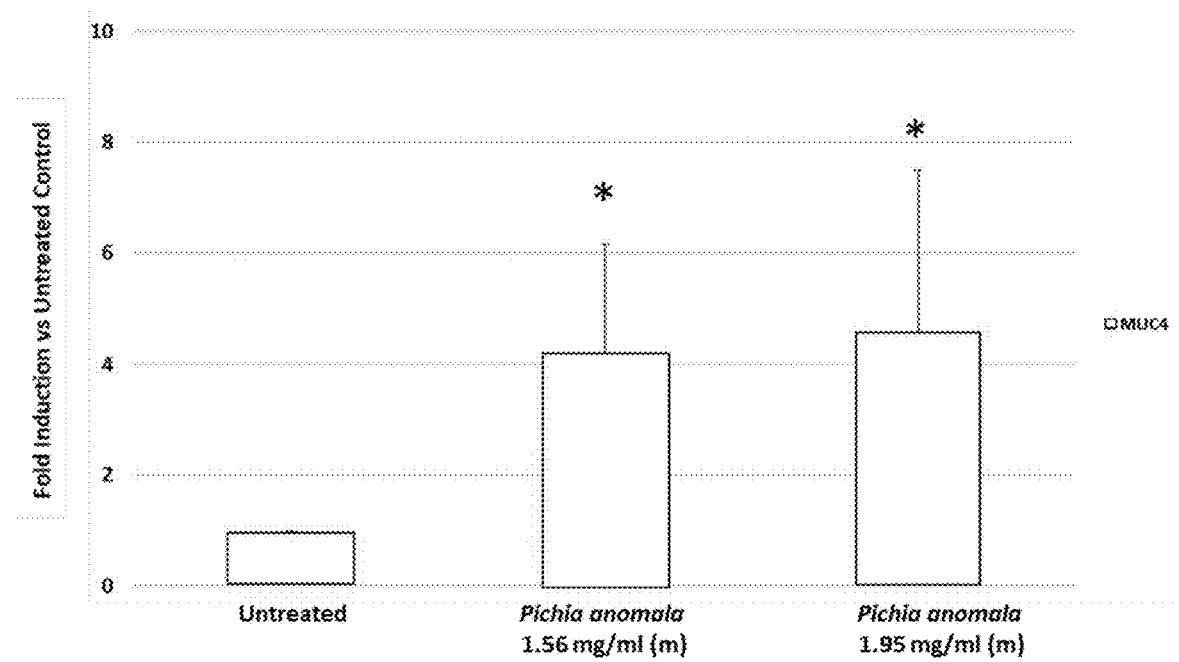
FIG. 1 depicts bar graphs showing increase in MUC4 expression in corneal epithelial cells after adding *Pichia anomala* extract to growth medium containing corneal epithelial cells.

It is believed that one skilled in the art can, based upon the description herein, utilize this invention to its fullest extent. The following specific embodiments can be construed as merely illustrative, and not limitative of the remainder of the disclosure in any way whatsoever.

The compositions of the present invention can comprise, consist of, or consist essentially of the elements, steps and limitations of the invention described herein, as well any of the additional or optional ingredients, components, or limitations described herein.

The term "comprising" (and its grammatical variations) as used herein is used in the inclusive sense of "having" or "including" and not in the exclusive sense of "consisting only of" The terms "a" and "the" as used herein are understood to encompass the plural as well as the singular.

Unless defined otherwise, all technical and scientific terms used herein have the same meaning as commonly understood by one of ordinary skill in the art to which the invention belongs. Also, all publications, patent applications, patents, and other references mentioned herein are incorporated by reference in their entirety to the extent that they are not inconsistent with this specification. As used herein, all percentages are by weight of the total composition unless otherwise specified As used herein, the terms "cornea" or "corneal" is, includes and/or relates to, the transparent front part of the eye that covers the iris, pupil, and anterior chamber, the layers of which transparent front part include the corneal epithelium layer (comprising corneal epithelial cells), Bowman's layer (also known as the anterior limiting membrane), Corneal stroma (also substantia propria), Descemet's membrane (also posterior limiting membrane), and Corneal endothelium (simple squamous or low cuboidal monolayer, approximately 5 µm thick, of mitochondria-rich cells).

The functions of the various layers are as follows:

Epithelium provides:
provides barrier to chemicals and water;
provides barrier to microbes;
provides smooth optical surface as an internal part of the tear film-cornea interface, contributing to refractive poser of the eye; and
houses Langerhans cells which perform important immunological functions.

Bowman's layer:
aides in maintaining the corneal shape.

Corneal stroma:
provides mechanical strength to cornea;
provides transparency of cornea; and
acts as refracting lens.

Descemet's membrane:
acts as resting layer for endothelial cells.

Corneal endothelium:
maintains corneal clarity by removing water from the corneal stroma.

The corneal epithelium layer is composed fairly uniformly of 5-7 layers of cells. The corneal epithelium is about 50µ in thickness. The epithelium is uniform to provide a smooth regular surface and is made up of nonkeratinized stratified squamous epithelium. Without being limited by theory, it is believed that, in the case of hyaluronic acid production, the corneal epithelium layer further contains tight junction structures (i.e., those structures [e.g., membrane or film barriers] typically inhibiting chemical permeation into tissues) which may obstruct, or act as a barrier, to diffusion of the one or more extracts, or sources of extracts, of the genus *Pichia*, reducing diffusion of the one or more extracts, or sources of extracts, of the genus *Pichia* across the corneal epithelium and into the corneal tissues, thereby, reducing the concentration levels of the extract that can accumulate within the corneal tissues and contact the cellular portions of such tissues responsible for hyaluronic acid production.

As used herein, the phrase "decreased or low-level production/release/delivery/excretion of hyaluronic acid from and/or in the cornea" means a concentration of hyaluronic acid which is less than the concentration of hyaluronic acid in the tears of a normal (i.e., non-diseased) person, or, in certain embodiments, less than 25 (or about 25) nanograms per milligram of proteins, as determined using the method described in Dreyfuss J L, Regatieri C V, Coelho B, et al. Altered hyaluronic acid content in tear fluid of patients with adenoviral conjunctivitis. An Acad Bras Cienc. 2015; 87(1): 455-462. That method (the Dreyfuss Method) is reproduced below:

Sample Collection
For collecting the tears, Schirmer strips were placed in the temporal side of each eye under the eyelid, during 5 minutes, without any use of topical anesthetics. The strips were dried at room temperature and stored at −20° C. until analysis.

Tear Sample Preparation
Tear compounds were eluted from the Schirmer strips using 100 µL of distilled water, and hyaluronic acid and protein content analyses were performed.

Hyaluronic Acid Measurement
Hyaluronic acid content in tear fluids was assayed by a non-isotopic fluoroassay (See Martins Jr, Passerotti C C, Maciel R M, Sampaio Lo, Dietrich C P and Nader H B. 2003.) Practical determination of hyaluronan by a new noncompetitive fluorescence-based assay on serum of normal and cirrhotic patients. Anal Biochem 319: 65-72.) Eluted tear fluids and standard concentrations of hyaluronic acid (Sigma, St. Louis, Mo.) were added to 96 multiwell plates (FluoroNUNC Maxisorp-microtiterplates, Roskilde, Denmark) previously coated with hyaluronic acid-binding protein. The plates were then sequentially incubated with biotinylated hyaluronic acid-binding protein and europiumlabeled streptavidin (Amershan, Piscataway, N.J.). Afterwards, the europium remaining in the solid phase was released by an enhancement solution and the fluorescence was measured using a time-resolved flurometer (Perkin-Elmer Life Sciences-Wallac Oy, Turku, Finland). The data (counts/s) were processed automatically using the MultiCalc software program (Perkin-Elmer Life Sciences-Wallac Oy) and values are expressed as ng/mg protein.

Protein Analysis
Total tear protein concentration was determined using a colorimetric assay kit according to the manufacturer's instructions (Protein Assay Kit from Bio-Rad, Hercules, Calif.). The protein profile was analyzed through sodium dodecylsulfate polyacrylamide gel electrophoresis (SDS-PAGE) as previously described (See Laemmli U K. 1970.) Cleavage of structural proteins during the assembly of the head of bacteriophage T4. Nature 227: 680-685.). Briefly, 10 µg of protein from the tear samples were applied to a 3-20% linear gradient polyacrylamide gel under reducing conditions. After electrophoresis, the gels were stained by comassie blue (Bio-Rad, Hercules, Calif.). Each protein band was quantified by densitometry using the software ImageJ Version 10.2 for Mac (U.S. National Institutes of Health, Bethesda, Md., USA). The results are expressed by arbitrary densitometric units (ADU).

As used herein, the phrase "decreased or low-level production/release/delivery/excretion of mucin from and/or in the cornea" means a concentration of MUC5AC which is less than the concentration of MUC5AC in the tears of a normal (i.e., non-diseased) person, or, in certain embodiments, less than 6, optionally less than 8, nanograms per milligram of proteins, as determined using the method described in Uchino Y, Uchino M, Yokoi N, et al. Alteration of Tear Mucin 5AC in Office Workers Using Visual Display Terminals: The Osaka Study. *JAMA Ophthalmol.* n2014; 132(8):985-992. That method (the Uchino Method) is reproduced below:

MUC5AC Concentration in Tears
The concentration of the secreted mucin MUC5AC in the tear samples was quantified by enzyme-linked immunoassay (E90756Hu; USCN Life Science). (See Maker A V, Katabi N, Gonen M, et al. Pancreatic cyst fluid and serum mucin levels predict dysplasia in intraductal mucinous neoplasms of the pancreas. *Ann Surg Oncol.* 2011; 18(1):199-206.) All samples were analyzed according to the manufacturer's guidelines. Absorbance was measured at 450 nm, and the standard solutions in the kit were recombinant human MUC5AC. A protein assay reagent kit (BCA Protein Assay Pierce) was used to determine the protein concentration in the tear samples. The MUC5AC concentration was normalized to the tear protein content and expressed as MUC5AC protein (nanograms) per tear total protein (milligrams).

As used herein, a composition that is "essentially free" of an ingredient means the composition that has about 2% or less of that ingredient by weight based on the total weight of the composition. Preferably, a composition that is essentially free of an ingredient has about 1% or less, more preferably about 0.5% or less, more preferably about 0.1% or less, more preferably about 0.05 or less, more preferably about 0.01% or less by weight based on the total weight of composition of the ingredient. In certain more preferred embodiments, a composition that is essentially free of an ingredient is free of the ingredient, i.e. has none of that ingredient in the composition.

As used herein, "microemulsion" means emulsions possessing one or more of the following characteristics: i) they are formed spontaneously or substantially spontaneously when their components are brought into contact, that is without substantial energy supply, e.g. in the absence of heating or the use of high shear equipment or other substantial agitation; ii) they exhibit thermodynamic stability; iii) they are monophasic; iv) they are substantially non-opaque, i.e. are transparent or opalescent when viewed by optical microscopic means; and/or v) in their undisturbed state, they are optically isotropic, though an anisotropic structure may be observable using e.g. x-ray technique. The particles of a microemulsion may be spherical, though other structures are feasible, e.g. liquid crystals with lamellar, hexagonal or isotropic symmetries. Generally, microemulsions comprise droplets or particles having a maximum dimension (e.g. diameter) of less than 1,500 Å, preferably less than 1000 Å, preferably less than 500 Å, but greater than 100 Å. Included within this definition of microemulsion are self-emulsifying drug delivery systems (SEDDS). SEDDS are isotropic mixtures of oil, surfactant (with or without co-surfactant) and co-solvent which spontaneously emulsify when exposed to an aqueous medium with gentle agitation. SEDDS may be used to improve bioavailability of poorly water soluble drugs via oral administration. The addition of a co-solvent facilitate the formation of a self-emulsifying system as it significantly reduces the interfacial tension. In so doing, it creates a fluid interfacial film with sufficient flexibility to take up different curvatures required to form microemulsion over a wide range of compositions. Further detail regarding SEDDS can be found in US Pat. Publication US2018/0036233A1 to Shabaik et al., herein incorporated by reference in its entirety.

As used herein, "ophthalmologically acceptable" means that the ingredients which the term describes are suitable for use in contact with tissues (e.g., the soft tissues of the eye or periorbital skin tissues) without undue toxicity, incompatibility, instability, irritation, allergic response, and the like. As will be recognized by one of skill in the art, cosmetically/dermatologically acceptable salts are acidic/anionic or basic/cationic salts.

As used herein, the term "safe and effective amount" means an amount of disclosed the extract, compound or of the composition sufficient to induce, promote and/or improve the production/release/delivery/excretion of hyaluronic acid and/or mucin from and/or in one or more layer of the cornea, but low enough to avoid serious side effects. The safe and effective amount of the compound, extract, or composition will vary with e.g. the age, health and environmental exposure of the end user, the duration and nature of the treatment, the specific extract, ingredient, or composition employed, the particular ophthalmologically-acceptable carrier utilized, and like factors.

In certain embodiments, the present invention as disclosed herein may be practiced in the absence of any compound or element (or group of compounds or elements) which is not specifically disclosed herein.

In general, IUPAC nomenclature rules are used herein and according to the following term definitions.

The term "C1-8 alkyl," whether used alone or as part of a substituent group, refers to a saturated aliphatic branched or straight-chain monovalent hydrocarbon radical having from 1-8 carbon atoms. For example, "C1-8alkyl" specifically includes the radicals methyl, ethyl, 1-propyl, 2-propyl, 1-butyl, 2-butyl, tert-butyl, 1-butyl, 1-pentyl, 2-pentyl, 3-pentyl, 1-hexyl, 2-hexyl, 3-hexyl, 1-heptyl, 2-heptyl, 3-heptyl, 1-octyl, 2-octyl, 3-octyl and the like. Said term may also refer to the corresponding alkyldiyl radical. Alkyl and alkyldiyl radicals may be attached to a core molecule via a terminal carbon atom or via a carbon atom within the chain. Similarly, any number of substituent variables may be attached to an alkyl or alkyldiyl radical when allowed by available valences.

The term "$C_{1-4}$alkyl," whether used alone or as part of a substituent group, refers to a saturated aliphatic branched or straight-chain monovalent hydrocarbon radical or alkyldiyl linking group having a specified number of carbon atoms, wherein the radical is derived by the removal of one hydrogen atom from a carbon atom and the alkyldiyl linking group is derived by the removal of one hydrogen atom from each of two carbon atoms in the chain. The term "$C_{1-4}$alkyl" refers to a radical having from 1-4 carbon atoms in a linear or branched arrangement. For example, "$C_{1-4}$alkyl" specifically includes the radicals methyl, ethyl, 1-propyl, 2-propyl, 1-butyl, 2-butyl, tert-butyl, 1-butyl, and the like. Alkyl and alkyldiyl radicals may be attached to a core molecule via a terminal carbon atom or via a carbon atom within the chain. Similarly, any number of substituent variables may be attached to an alkyl or alkyldiyl radical when allowed by available valences.

The term "$C_{2-4}$alkenyl" refers to an alkenyl radical having from 2-4 carbon atoms. For example, specifically includes the radicals ethenyl, propenyl, allyl (2-propenyl), butenyl and the like. As described above, an alkenyl radical may be similarly attached to a core molecule and further substituted where indicated.

The term "halo" as such or in combination with other terms means halogen atom, such as fluoro, chloro, bromo or iodo.

The term "substituted," refers to a core molecule in which one or more hydrogen atoms have been replaced with that amount of substituents allowed by available valences. Substitution is not limited to the core molecule, but may also occur on a substituent radical, whereby the radical becomes a linking group.

The term "independently selected" refers to two or more substituents that may be selected from a substituent variable group, wherein the selected substituents may be the same or different.

The term "dependently selected" refers to one or more substituent variables that are specified in an indicated combination for substitution in a core molecule (e.g. variables that refer to groups of substituents appearing in a tabular list of compounds).

Acceptable salts from inorganic bases include, for example, sodium or potassium salts, and the like. Acceptable salts from organic bases include, for example, salts formed with primary, secondary, or tertiary amines, and the like.

Compounds and/or Extracts which Induce, Promote and/or Improve Production/Release/Delivery/Excretion of Hyaluronic Acid and/or Mucin in the Cornea.

The present invention comprises one or more compounds and/or extracts which induce, promote and/or improve production/release/delivery/excretion of hyaluronic acid and/or mucin from and/or in the cornea.

In certain embodiments, the compounds and/or extracts which induce, promote and/or improve production/release/delivery/excretion of hyaluronic acid and/or mucin from and/or in the cornea are, or comprise, extracts, or sources of extracts, of the genus *Pichia*.

*Pichia* is a genus of yeasts in the family Saccharomycetaceae. More than 100 species of this genus are known. Suitable species for use in the compositions of the present invention include (selected from or selected from the group consisting of) *Pichia anomala, Pichia guilliermondii Pichia norvegensis*, and *Pichia ohmeri. Pichia anomala* (formerly named *Hansenula anomala*) can be found in raw milk and cheese. The extracts of yeasts of the genus *Pichia* are rich in mannans, polysaccharides composed of mannose monomers. Extracts or sources of extracts of the genus *Pichia* may be isolated from the fruit or other aerial parts of a plant. Any ophthalmologically acceptable extract of the genus of *Pichia* may be used. Mixtures of extracts, or sources of extract, of the above species from the genus of *Pichia* may also be used.

In certain embodiments, the extracts, or sources of extracts, from genus of *Pichia* used in the present invention are extracts of *Pichia anomala*. Extracts of *Pichia anomala* can be isolated from the fruit or other aerial parts of a plant. In certain embodiments, a suitable extract of *Pichia anomala* is produced from a strain of *Pichia anomala* present on fruit or leaves of a kiwi plant. In another embodiment, extract of *Pichia anomala* is commercially available from Silab-France as PRO-LIPISKIN or UNFLAMAGYL®, where the extract is produced from a strain of *Pichia anomala* present on sugar cane. Preferred for use herein is an extract of *Pichia anomala* characterized as having:

a solids content of between 26 and 40 g/l,
a pH between 6 and 7,
a protein content between 2 and 170 g/l, and
a sugars content (mannose curve) ranging between 18 and 30 g/l (within which characterization falls PRO-LIPISKIN and Hyalurodine (Silab-France). Hyalurodine is the *Pichia anomala* extract used in the Examples (below). In one embodiment, the *Pichia anomala* extract is obtained in accordance with the following process as described in FR2897266 and FR2938768, both of which are incorporated by herein by reference.

In certain embodiments, the extraction process described below eliminates much of the protein from a *Pichia* extract and concentrates the active in terms of mannan. The process comprises at least one enzymatic hydrolysis step of the proteins, to obtain peptides and small proteins and, in certain embodiments, a further step of removing these small peptides and proteins by filtration based on the selection of the size of such molecules.

In certain embodiments, the extracts of *Pichia* genus, including *Pichia anomala* extract, are obtained by an extraction process involving one or more hydrolysis enzyme (s) to hydrolyze proteins in *Pichia* genus, either successively or simultaneously.

In certain embodiments, enzymatic hydrolysis is used to break-down proteins in the extract of the *Pichia* genus into protein fractions having weight average molecular weights of less than 5000 Da. Suitable hydrolysis enzymes include, but is not limited to, at least one peptidase, in certain embodiments, chosen from papain, trypsin, chymotrypsin, subtilisin, pepsin, thermolysin, pronase, flavastacine, enterokinase, factor Xa protease, Turin, bromelain, proteinase K, genenase I, thermitase, carboxypeptidase A, carboxypeptidase B, collagenase or mixtures thereof.

In certain embodiments, the enzymes used to obtain the *Pichia* genus extract are inactivated prior to separation of the resulting soluble and insoluble phases.

In one embodiment, the *Pichia anomala* extract is characterized as having:

a solids content of between 5 and 300 g/l,
a pH between 4 and 9,
a protein content between 2 and 10, preferably 3-9, g/l, and
a sugars content (mannose curve) ranging between 1 and 100 g/l In certain embodiments, extract of *Pichia* genus comprises a mannan content of greater than or equal to 30% of the total weight of dried *Pichia* genus extract, or optionally at a mannan content of at least 50% by weight of the total weight of the dried *Pichia* genus extract.

In certain embodiments, the phase of *Pichia* genus extract is dried (and the solids content is measured) by passing the *Pichia* genus extract containing phase through oven heat of 105° C. (or about 105° C.) in the presence of sand until a constant weight is obtained/observed.

In certain embodiments, the solids (or dry matter) content of the dried extract of *Pichia* genus is between 10 and 200 g/l, or optionally between 26 and 40 g/l.

In certain embodiments, the pH measured by the potentiometric method at room temperature (25° C.) leads to values of between 4.5 and 8.5, optionally between 6.0 and 7.0.

Determination of total sugar content, the DUBOIS method can be used. In the presence of concentrated sulphuric acid and phenol, reducing sugars give an orange yellow compound. From a standard range (preferably using a mannose assay curve), the total sugar content of a sample can be determined. In certain embodiments, the total sugar content in the dried extract of *Pichia* genus is between 7 and 145 g/l, or optionally between 18 and 29 g/l. In certain embodiments, the dried extract of *Pichia* genus contains at least 30% of total sugars by weight of dried extract of *Pichia* genus compared to the total solids by weight of dried extract of *Pichia* genus, optionally, at least 50% by weight of dried extract of *Pichia* genus.

In certain embodiments, the carbohydrate fraction of the dried extract of *Pichia* genus is composed of mannose and glucose in the form of (or essentially in the form of) oligosaccharides and polysaccharides having a weight average molecular weight of from about 180 to about 800,000 Da, optionally, from about 5000 to about 515,000 Da, optionally from about 6000 to about 270,000 Da. In certain embodiments, at least 70% (or about 70%), optionally at least 75% (or about 75%), at least 80% (or about 80%), optionally at least 85% (or about 85%), at least 90% (or about 90%), optionally at least 95% (or about 95%), or 100% (or about 100%) of the oligosaccharides and polysaccharides in the dried extract of *Pichia* genus fall within the aforementioned weight average molecular weight ranges.

Determination of the protein content protein is obtained by the Kjedhal method. In certain embodiments, the dried extract of *Pichia* genus has a protein content of between 4 and 90 g/l, or optionally between 12 and 18 g/l. The dried extract of *Pichia* genus contains less than 45% of proteins, or optionally less than 30%, of the total solids in the dried extract of *Pichia* genus.

In certain embodiments, the dried extract of *Pichia* genus comprises mannans, mannoses polymerized in the form of oligosaccharides and polysaccharides, whose weight average molecular weight is from about 180 to about 800,000 Da, optionally, from about 5000 to about 515,000 Da, optionally from about 6000 to about 270,000 Da. dried extract of *Pichia* genus. In certain embodiments, at least 70% (or about 70%), optionally at least 75% (or about 75%), at least 80% (or about 80%), optionally at least 85% (or about 85%), at least 90% (or about 90%), optionally at least 95% (or about 95%), or 100% (or about 100%) of the oligosaccharides and polysaccharides in the dried extract of *Pichia* genus fall within the aforementioned weight average molecular weight ranges.

In certain embodiments, the extraction process includes a step, after the step of enzymatic hydrolysis of proteins, of removing (e.g., through filtration) proteins having a weight average molecular weight of less than 5000 Da. Accordingly, the extracts of the *Pichia* genus are free of or substantially free of proteins and/or peptides having a weight average molecular weight of less than 5000 Da.

In certain embodiments, the above described extraction process may include a step of deodorizing, bleaching and/or stabilizing the extract of *Pichia* genus before the filtrations. The filtrations can be the following: —Press filtration, and —sterilizing filtration.

In certain embodiments, the extracts used belong to the variety *Pichia anomala*. A particular non-limiting example of a production process is described below.

Extracts (or yeasts) of *Pichia anomala* are cultured in a culture medium adapted to their development, then centrifuged to recover the biomass, The biomass is then milled in a ball mill. Then the ground material is resuspended in water at a concentration of 50 grams per liter before enzymatic hydrolysis in basic medium at 30° C. for 6 hours, After hydrolysis, the product is centrifuged and filtered before sterilization, By successive filtrations on filters of different sizes, a hydrolyzate containing at least 30% of mannans relative to the total weight of the solids is obtained and/or proteins of specific weight average molecular weight are obtained. (The hydrolyzate obtained is in the form of a clear liquid aqueous solution of light yellow color.)

In certain embodiments, the *Pichia anomala* extract is obtained in accordance with the following manufacturing examples:

1. *Pichia anomala* extract A:
    I. Extraction of the *Pichia anomala* extract A:
        Preparation of *Pichia anomala* extract A includes the following steps:
            culture of yeast *Pichia anomala* in an environment adapted to their development,
            centrifugation to retrieve the biomass,
            solubilization of biomass,
            enzymatic hydrolysis at basic pH,
            separation of the soluble and insoluble phases,
            heat treatment,
            filtration, and
            sterile filtration.
    II. Characterization of the *Pichia anomala* extract A:
        The *Pichia anomala* extract A obtain above is characterized by:
            a solids content of between 48 and 84 g/l,
            a pH between 4 and 9,
            a protein content between 19 and 48 g/l, and
            a total sugar content between 10 and 42 g/l.
2. *Pichia anomala* extract B
    I. Extraction of the *Pichia anomala* extract B:
        Preparation of *Pichia anomala* extract B includes the following steps:
            culture of yeast *Pichia anomala* in an environment adapted to their development,
            centrifugation to retrieve the biomass,
            solubilization of biomass,
            enzymatic hydrolysis at acid pH,
            separation of the soluble and insoluble phases,
            heat treatment,
            filtration, and
            sterile filtration.
    II. Characterization of the *Pichia anomala* extract B:
        The *Pichia anomala* extract B obtain above is characterized by:
            a solids content of between 58 and 95 g/l,
            a pH between 4 and 9,
            a protein content between 23 and 54 g/l, and
            a total sugar content between 12 and 32 g/l.
3. *Pichia anomala* extract C
    I. Extraction of the *Pichia anomala* extract C:
        Preparation of *Pichia anomala* extract C includes the following steps:
            culture of yeast *Pichia anomala* in an environment adapted to their development,
            centrifugation to retrieve the biomass,
            solubilization of biomass,
            successive enzymatic hydrolyses in basic medium,
            separation of the soluble and insoluble phases,
            heat treatment,
            filtration, and
            sterile filtration.
    II. Characterization of the *Pichia anomala* extract C:
        The *Pichia anomala* extract C obtain above is characterized by:
            a solids content of between 91 and 195 g/l,
            a pH between 4 and 9,
            a protein content between 36 and 111 g/l, and
            a total sugar content between 18 and 65 g/l.
4. *Pichia anomala* extract D
    I. Extraction of the *Pichia anomala* extract D:
        Preparation of *Pichia anomala* extract D includes the following steps:
            culture of yeast *Pichia anomala* in an environment adapted to their development,
            centrifugation to retrieve the biomass,
            solubilization of biomass,
            hydrolyzed simultaneously with at least two enzymes at acid pH,
            separation of the soluble and insoluble phases,
            heat treatment,
            filtration, and
            sterile filtration.

II. Characterization of the *Pichia anomala* extract D:
The *Pichia anomala* extract D obtain above is characterized by:
a solids content of between 5 and 53 g/l,
a pH between 4 and 9,
a protein content between 2 and 30 g/l, and
a total sugar content between 1 and 18 g/l.

5. *Pichia anomala* extract E
I. Extraction of the *Pichia anomala* extract E:
Preparation of *Pichia anomala* extract E includes the following steps:
culture of yeast *Pichia anomala* in an environment adapted to their development,
centrifugation to retrieve the biomass,
solubilization of biomass in a hydroglycolique environment,
hydrolyzed simultaneously with at least two enzymes at acid pH,
separation of the soluble and insoluble phases,
heat treatment,
filtration, and
sterile filtration.
II. Characterization of the *Pichia anomala* extract E:
The *Pichia anomala* extract E obtain above is characterized by:
a solids content of between 172 and 300 g/l,
a pH between 4 and 9,
a protein content between 69 and 170 g/l, and
a total sugar content between 34 and 100 g/l.

Preferably, the *Pichia anomala* extract is obtained using the process for obtaining *Pichia anomala* extract D as described above.

In certain embodiments, the extract, or source of extracts, of the genus *Pichia* comprises oligosaccharides and polysaccharides having an average degree of polymerization of from DP 1 to DP 4444, optionally from DP 30 to DP 2860, optionally from DP 35 to DP 1500. In certain embodiments, at least 70% (or about 70%), optionally at least 75% (or about 75%), at least 80% (or about 80%), optionally at least 85% (or about 85%), at least 90% (or about 90%), optionally at least 95% (or about 95%), or 100% (or about 100%) of the oligosaccharides and polysaccharides in the dried extract of *Pichia* genus fall within the aforementioned average degree of polymerization ranges.

In certain embodiments, the extract, or source of extracts, of the genus *Pichia* are present in the compositions of the present invention so as to provide a *Pichia* extract concentration in, or contacting, corneal tissue cells in the user (i.e., internal corneal fluid levels), after topical application, of at least 0.3 mg/ml (or about 0.3 mg/ml), optionally, at least 0.5 mg/ml (or about 0.5 mg/ml), optionally, at least 1 mg/ml (or about 1 mg/ml), optionally, at least 1.5 mg/ml (or about 1.5 mg/ml), optionally, at least 2 mg/ml (or about 2 mg/ml), optionally, at least 2.5 mg/ml (or about 2.5 mg/ml), optionally, at least 3 mg/ml (or about 3 mg/ml), optionally, at least 3.5 mg/ml (or about 3.5 mg/ml), optionally, at least 4 mg/ml (or about 4 mg/ml), optionally, at least 4.5 mg/ml (or about 4.5 mg/ml), optionally, at least 5 mg/ml (or about 5 mg/ml), or at least 5.5 mg/ml (or about 5.5 mg/ml), optionally, at least 6 mg/ml (or about 6 mg/ml), or optionally, at least 6.5 mg/ml (or about 6.5 mg/ml), optionally, at least 7 mg/ml (or about 7 mg/ml), optionally, at least 7.5 mg/ml (or about 7.5 mg/ml), optionally, at least 8 mg/ml (or about 8 mg/ml), optionally, at least 8.5 mg/ml (or about 8.5 mg/ml), optionally, at least 9 mg/ml (or about 9 mg/ml), optionally, at least 8.5 mg/ml (or about 8.5 mg/ml), optionally, at least 9 mg/ml (or about 9 mg/ml), optionally, at least 9.5 mg/ml (or about 9.5 mg/ml), or optionally, at least 10 mg/ml (or about 10 mg/ml) to 100 mg/ml (or about 100 mg/ml), optionally, to 95 mg/ml (or about 95 mg/ml), optionally, to 90 mg/ml (or about 90 mg/ml), optionally, to 85 mg/ml (or about 85 mg/ml), optionally, to 80 mg/ml (or about 80 mg/ml), optionally, to 75 mg/ml (or about 75 mg/ml), optionally, to 70 mg/ml (or about 70 mg/ml), optionally, to 65 mg/ml (or about 65 mg/ml), optionally, to 60 mg/ml (or about 60 mg/ml), optionally, to 55 mg/ml (or about 55 mg/ml), optionally, to 50 mg/ml (or about 50 mg/ml), optionally, to 45 mg/ml (or about 45 mg/ml), optionally, to 40 mg/ml (or about 40 mg/ml), optionally, to 35 mg/ml (or about 35 mg/ml), optionally, to 30 mg/ml (or about 30 mg/ml), optionally, to 25 mg/ml (or about 25 mg/ml), optionally, to 20 mg/ml (or about 20 mg/ml), or optionally, to 15 mg/ml (or about 15 mg/ml).

In certain embodiments, the extract, or source of extracts, of the genus *Pichia* are present in the compositions of the present invention at a concentration of from 0.01% (or about 0.01%), optionally, from 0.05% (or about 0.05%), optionally, from 0.1% (or about 0.1%), optionally, from 0.5% (or about 0.5%), optionally, from 1% (or about 1%), optionally, from 1.5% (or about 1.5%), optionally, from 2% (or about 2%), optionally, from 2.5% (or about 2.5%), optionally, from 3% (or about 3%), optionally, from 3.5%, (or about 3.5%), optionally, from 4% (or about 4%), optionally, from 4.5% (or about 4.5%), optionally, from 5% (or about 5%), optionally, from 5.5% (or about 5.5%), optionally, from 6% (or about 6%), optionally, from 6.5% (or about 6.5%), optionally, from 7% (or about 7%), optionally, from 7.5% (or about 7.5%), optionally, from 8% (or about 8%), optionally, from 8.5% (or about 8.5%), optionally, from 9% (or about 9%), optionally, from 9.5% (or about 9.5%), optionally, from 10% (or about 10%), optionally, from 10.5% (or about 10.5%), optionally, from 11% (or about 11%), optionally, from 11.5% (or about 11.5%), optionally, from 12% (or about 12%), optionally, from 12.5% (or about 12.5%), optionally, from 13% (or about 13%), optionally, from 13.5% (or about 13.5%), optionally, from 14% (or about 14%), optionally, from 14.5% (or about 14.5%), optionally, from 15% (or about 15%), optionally, from 15.5% (or about 15.5%), optionally, from 16% (or about 16%), optionally, from 16.5% (or about 16.5%), optionally, from 17% (or about 17%), optionally, from 17.5% (or about 17.5%), optionally, from 18% (or about 18%), optionally, from 18.5% (or about 18.5%), optionally, from 19% (or about 19%), optionally, from 19.5% (or about 19.5%), optionally, from 20% (or about 20%), optionally, from 20.5% (or about 20.5%) to 30% (or about 30%), optionally, to 35% (or about 35%), optionally, to 40% (or about 40%), optionally, to 45% (or about 45%), optionally, to 50% (or about 50%), optionally, to 55% (or about 55%), optionally, to 60% (or about 60%), optionally, to 65% (or about 65%), optionally, to 70% (or about 70%), optionally, to 75% (or about 75%), optionally, to 80% (or about 80%), optionally, to 85% (or about 85%), optionally, to 90% (or about 90%), optionally, to 95% (or about 95%), or optionally, to 100% (or about 100%), by weight, of the total composition.

Permeation Enhancer

In certain embodiments, the compositions of the present invention optionally comprise a permeation enhancer.

Suitable permeation enhancers include (selected from or selected from the group consisting of) either alone or in combination, surfactants such as saponins, polyoxyethylene, polyoxyethylene ethers of fatty acids such as polyoxyethylene 4-, 9-, 10-, and 23-lauryl ether, polyoxyethylene 10- and 20-cetyl ether, polyoxyethylene 10- and 20-stearyl ether, sorbitan monooleate, sorbitan monolaurate, polyoxyethylene monolaurate, polyoxyethylene sorbitans such as polyoxyethylene sorbitan monolaurate, decamethonium, decamethonium bromide, and dodecyltrimethylammonium bromide; chelators such natural polyacids (e.g., citric acid), phosphate salts (e.g., disodium pyrophosphate), phosphonates, bisphosphonates (e.g., etridronic acid), aminocarboxylic acids (e.g., ethylenediaminetetraacetic acid (EDTA) and disodium EDTA) and ethylenediamine-N,N'-disuccinic acid (EDDS)); bile salts and acids such as cholic acid, deoxycholic acid, glycocholic acid, glycodeoxycholic acid, taurocholic acid, taurodeoxycholic acid, sodium cholate, sodium glycocholate, glycocholate, sodium deoxycholate, sodium taurocholate, sodium glycodeoxycholate, sodium taurodeoxycholate, chenodeoxycholic acid, and urosdeoxycholic acid; fusidic acid derivatives, glycyrrhizic acid, and ammonium glycyrrhizide, with saponin EDTA, fusidic acid, polyoxyethylene 9-lauryl ether, polyoxyethylene 20-stearylether, glycocholate, or mixtures of any of the above.

The concentration of permeation enhancer administered should be the minimum amount needed to sufficiently increase absorption of the compound and/or extract through the mucous or other barrier membranes of the eye. Generally, concentrations ranging from 0.01% (or about 0.01%), optionally, from 0.05% (or about 0.05%), optionally, from 0.1% (or about 0.1%), optionally, from 0.15% (or about 0.15%), optionally, from 0.2% (or about 0.2%), optionally, from 0.25% (or about 0.25%) to 2% (or about 2%), optionally, to 2.5% (or about 2.5%), optionally, to 3% (or about 3%), optionally, to 3.5%, (or about 3.5%), optionally, to 4% (or about 4%), optionally, to 4.5% (or about 4.5%), optionally, to 5% (or about 5%), optionally, to 5.5% (or about 5.5%), optionally, to 6% (or about 6%), optionally, to 6.5% (or about 6.5%), optionally, to 7% (or about 7%), optionally, to 7.5% (or about 7.5%), optionally, to 8% (or about 8%), optionally, to 8.5% (or about 8.5%), optionally, to 9% (or about 9%), optionally, to 9.5% (or about 9.5%), optionally, to 10% (or about 10%), optionally, to 10.5% (or about 10.5%), optionally, to 11% (or about 11%), optionally, to 11.5% (or about 11.5%), optionally, to 12% (or about 12%), optionally, to 12.5% (or about 12.5%), optionally, to 13% (or about 13%), optionally, to 13.5% (or about 13.5%), optionally, to 14% (or about 14%), optionally, to 14.5% (or about 14.5%), optionally, to 15% (or about 15%), optionally, to 15.5% (or about 15.5%), optionally, to 16% (or about 16%), optionally, to 16.5% (or about 16.5%), optionally, to 17% (or about 17%), optionally, to 17.5% (or about 17.5%), optionally, to 18% (or about 18%), optionally, to 18.5% (or about 18.5%), optionally, to 19% (or about 19%), optionally, to 19.5% (or about 19.5%), optionally, to 20% (or about 20%), of the total composition (w/v), are useful in the compositions of the present invention.

Ophthalmologically Acceptable Carrier

The compositions of the present invention also comprise an aqueous, oil-in-water emulsion, water-in-oil emulsion carrier, oil-in-water microemulsion, or water-in-oil microemulsion carrier. The carrier is ophthalmologically acceptable. Useful oil-in-water and water-oil-carriers can be found in US Patent Publication 20030165545A1 and U.S. Pat. Nos. 9,480,645, 8,828,412 and 8,496,976, each of which patent documents are herein incorporated by reference in its entirety.

In certain embodiments, the compositions of the present invention include emulsions, optionally, self-emulsifying emulsions, including an oily component, such as one or more oils, for example, and without limitation, mineral oil and/or one or more other conventional well known and/or commercially available oils suitable for use in the present invention; a surfactant component which includes three or more surfactants; and an aqueous component which includes an aqueous phase. In addition, a number of additional components may be included in the present compositions. The compositions of the present invention are substantially non-toxic and/or non-irritating and/or non-damaging to the eye and can provide a protective function for ocular cells and tissues.

One or more oils or oily substances are used to form the present compositions. Any suitable oil or oily substance or combinations of oils or oily substances may be employed provided such oils and/or oily substances are effective in the present compositions, and do not cause any substantial or significant detrimental effect to the human or animal to whom the composition is administered, or to the contact lens being treated, or the wearing of the treated contact lens, or to the wearer of the treated contact lens. The oily component may, for example, and without limitation, be a higher fatty acid glyceride, for example, castor oil, corn oil, sunflower oil and the like and mixtures thereof. The oily component may include one or more non-polar oils such as mineral oil, silicone oil and the like and mixtures thereof.

The ophthalmologically acceptable carrier (or, compositions of the present invention) may optionally comprise one or more additional excipients and/or one or more additional active ingredients. Examples of such optional components are described below.

Excipients commonly used in ophthalmic compositions include, but are not limited to, demulcents, tonicity agents, preservatives, chelating agents, buffering agents (other than and in addition to the organic acids of the present invention), and surfactants. Other excipients comprise solubilizing agents, stabilizing agents, comfort-enhancing agents, polymers, emollients, pH-adjusting agents (other than and in addition to the organic acids of the present invention), and/or lubricants. Any of a variety of excipients may be used in the compositions of the present invention including water, mixtures of water and water-miscible solvents, such as vegetable oils or mineral oils comprising from 0.5% to 5% non-toxic water-soluble polymers, natural products, such as agar and acacia, starch derivatives, such as starch acetate and hydroxypropyl starch, and also other synthetic products such as polyvinyl alcohol, polyvinylpyrrolidone, polyvinyl methyl ether, polyethylene oxide, and preferably cross-linked polyacrylic acid and mixtures thereof.

Demulcents or soothing agents used with embodiments of the present invention include, but are not limited to, cellulose derivatives (such hydroxyethyl cellulose, methyl cellulose, hypromellose or mixtures thereof), hyaluronic acid or salt thereof (such as sodium hyaluronate), tamarind seed extract, glycerin, polyvinyl pyrrolidone, polyethylene oxide, polyethylene glycol, propylene glycol and polyacrylic acid and mixtures thereof. In certain embodiments, one or more of hyaluronic acid, propylene glycol, tamarind seed extract, glycerin and/or polyethylene glycol 400 are the demulcents or soothing agents. In certain embodiments, the demulcent or soothing agent is selected from hyaluronic acid, tamarind seed extract or mixtures thereof.

Compositions of the present invention are ophthalmologically suitable for application to a subject's eyes. The term "aqueous" typically denotes an aqueous formulation wherein the excipient is >about 50%, more preferably >about 75% and in particular >about 90% by weight water. In certain embodiments, the compositions of the present invention are essentially free of compounds which irritate the eye. In certain embodiments, the compositions of the present invention are essentially free of free fatty acids and $C_1$ to $C_4$ alcohols. In certain embodiments, the compositions of the present invention are comprise less than 40% (or about 40%), optionally, less than 35% (or about 35%), optionally, less than 30% (or about 30%), optionally less than 25% (or about 25%), optionally, less than 20% (or about 20%), optionally, less than 15% (or about 15%), optionally less than 10% (or about 10%), or optionally, less than 5% (or about 5%), by weight of the total composition, of a non-alcohol, organic excipient or solvent. These drops may be delivered from a single dose ampoule which may preferably be sterile and thus render bacteriostatic components of the formulation unnecessary. Alternatively, the drops may be delivered from a multi-dose bottle which may preferably comprise a device which extracts any preservative from the composition as it is delivered, such devices being known in the art.

In certain embodiments, the compositions of the present invention are isotonic, or slightly hypotonic in order to combat any hypertonicity of tears caused by evaporation and/or disease. This may require a tonicity agent to bring the osmolality of the formulation to a level at or near 210-320 milliosmoles per kilogram (mOsm/kg). The compositions of the present invention generally have an osmolality in the range of 220-320 mOsm/kg, or, optionally, have an osmolality in the range of 235-300 mOsm/kg. The ophthalmic compositions will generally be formulated as sterile aqueous solutions.

The osmolality of the compositions of the present invention may be adjusted with tonicity agents to a value which is compatible with the intended use of the compositions. For example, the osmolality of the composition may be adjusted to approximate the osmotic pressure of normal tear fluid, which is equivalent to about 0.9 w/v % of sodium chloride in water. Examples of suitable tonicity adjusting agents include, without limitation, sodium, potassium, calcium and magnesium chloride; dextrose; glycerin; propylene glycol; mannitol; sorbitol and the like and mixtures thereof. In one embodiment, a combination of sodium chloride and potassium chloride are used to adjust the tonicity of the composition.

The compositions of the present invention can also be used to administer pharmaceutically active compounds. Such compounds include, but are not limited to, glaucoma therapeutics, pain relievers, anti-inflammatory and anti-allergy medications, and anti-microbials. More specific examples of pharmaceutically active compounds include betaxolol, timolol, pilocarpine, carbonic anhydrase inhibitors and prostglandins; dopaminergic antagonists; post-surgical antihypertensive agents, such as para-amino clonidine (apraclonidine); anti-infectives such as ciprofloxacin, moxifloxacin, and tobramycin; non-steroidal and steroidal anti-inflammatories, such as naproxen, diclofenac, nepafenac, suprofen, ketorolac, tetrahydrocortisol and dexamethasone; dry eye therapeutics such as PDE4 inhibitors; and anti-allergy medications such as H1/H4 inhibitors, H4 inhibitors, olopatadine or mixtures thereof.

It is also contemplated that the concentrations of the ingredients comprising the formulations of the present invention can vary. A person of ordinary skill in the art would understand that the concentrations can vary depending on the addition, substitution, and/or subtraction of ingredients in a given formulation.

In certain embodiments, the compositions of the present invention may have a pH which is compatible with the intended use, and is often in the range of 4 (or about 4) to 10 (or about 10), optionally between 6 (or about 6) to 8 (to about 8), optionally between 6.5 (or about 6.5) to 7.5 (or about 7.5), or optionally between 6.8 (or about 6.8) to 7.2 (or about 7.2).

In certain embodiments, a variety of conventional buffers may be employed, such as phosphate, borate, citrate, acetate, histidine, tris, bis-tris and the like and mixtures thereof. Borate buffers include boric acid and its salts, such as sodium or potassium borate. Potassium tetraborate or potassium metaborate, which produce boric acid or a salt of boric acid in solution, may also be employed. Hydrated salts such as sodium borate decahydrate can also be used. Phosphate buffers include phosphoric acid and its salts; for example, $M_2HPO_4$ and $MH_2PO_4$, wherein M is an alkali metal such as sodium and potassium. Hydrated salts can also be used. In one embodiment of the present invention, $Na_2HPO_4 \cdot 7H_2O$ and $NaH_2PO_2 \cdot H_2O$ are used as buffers. The term phosphate also includes compounds that produce phosphoric acid or a salt of phosphoric acid in solution. Additionally, organic counter-ions for the above buffers may also be employed. The concentration of buffer generally varies from about 0.01 to 2.5 w/v % and more preferably varies from about 0.05 to about 0.5 w/v %.

In certain embodiments, the viscosity of the compositions of the present invention range from about 1 to about 500 cps, optionally from about 10 to about 200 cps, or optionally from about 10 to about 100 cps, when measured using a TA Instrument AR 2000 rheometer. The TA Instrument AR 2000 rheometer should be used with the AR2000 flow test method of the TA Rheological Advantage software with a 40 mm steel plate geometry; the viscosity ranges should be obtained by measuring steady state flow controlling shear rate from 0 sec to 200 $sec^{-1}$.

In certain embodiments, the compositions of the present invention are useful as, and in the form of, eye-drop solution, eye wash solution, contact lens lubricating and/or rewetting solution, spray, mist or any other manner of administering a composition to the eye.

The compositions of the present invention may also be useful as, and in the form of, packing solutions for contact lenses. In certain embodiments, as packing solutions, the compositions of the present invention may be sealed in blister packaging and, also, suitable for undergoing sterilization.

Examples of blister packages and sterilization techniques are disclosed in the following references which are hereby incorporated by reference in their entirety, U.S. Pat. Nos. D435,966; 4,691,820; 5,467,868; 5,704,468; 5,823,327; 6,050,398, 5,696,686; 6,018,931; 5,577,367; and 5,488,815. This portion of the manufacturing process presents another method of treating the ophthalmic devices with anti-allergic agent, namely adding anti-allergic agents to a solution prior to sealing the package, and subsequently sterilizing the package. This is the preferred method of treating ophthalmic devices with anti-allergic agents.

Sterilization can take place at different temperatures and periods of time. The preferred sterilization conditions range from about 100° C. for about 8 hours to about 150° C. for about 0.5 minute. More preferred sterilization conditions range from about 115° C. for about 2.5 hours to about 130° C. for about 5.0 minutes. The most preferred sterilization conditions are about 124° C. for about 18 minutes.

When used as packing solutions, the compositions of the present invention may be water-based solutions. Typical packing solutions include, without limitation, saline solutions, other buffered solutions, and deionized water. In certain embodiments, the packing solution is an aqueous solution of deioinized water or saline solution containing salts including, without limitation, sodium chloride, sodium borate, sodium phosphate, sodium hydrogenphosphate, sodium dihydrogenphosphate, or the corresponding potassium salts of the same. These ingredients are generally combined to form buffered solutions that include an acid and its conjugate base, so that addition of acids and bases cause only a relatively small change in pH. In certain embodiments, the pH of the packing solution is as described above. The buffered solutions may additionally include 2-(N-morpholino)ethanesulfonic acid (MES), sodium hydroxide, 2,2-bis(hydroxymethyl)-2,2',2"-nitrilotriethanol, n-tris(hydroxymethyl)methyl-2-aminoethanesulfonic acid, citric acid, sodium citrate, sodium carbonate, sodium bicarbonate, acetic acid, sodium acetate, ethylenediamine tetraacetic acid and the like and combinations thereof. Preferably, the solution is a borate buffered or phosphate buffered saline solution or deionized water. The particularly preferred solution contains about 500 ppm to about 18,500 ppm sodium borate, most particularly preferred about 1000 ppm of sodium borate.

If any ingredients incorporated into the packing solutions are subject to oxidative degradation, agents that stabilize packing solutions containing such ingredients may be added. Such "oxidative stabilization agents" include but are not limited to chelants such as EDTA, Dequest, Desferal, silica, chitin derivatives such as chitosan, cellulose and its derivatives, and N,N,N',N',N",N"-hexa(2-pyridyl)-1,3,5-tris(aminomethyl)benzene, and certain macrocyclic ligands such as crown ethers, ligand containing knots and catenands. See, David A. Leigh et al Angew. Chem Int. Ed., 2001, 40, No. 8, pgs. 1538-1542 and Jean-Claude Chambron et al. Pure & Appl. Chem., 1990, Vol. 62, No. 6, pgs. 1027-1034. Oxidative stabilization agents may include other compounds that inhibit oxidations such as those selected from the group consisting of 2,2',2",6,6',6"-Hexa-(1,1-dimethylethyl)4,4', 4"-[(2,4,6-trimethyl-1,3,5-benzenetriyl)-trismethylene]-triphenol (Irganox 1330), 1,3,5tris[3,5-di(1,1-dimethylethyl)4-hydroxybenzyl]-1H,3H,5H-1,3,5-triazine-2,4,6-trione, pentaerythrityl tetrakis[3-[3,5-di(1,1-dimethylethyl)-4-hydroxyphenyl]-propionate], octadecyl-3-[3,5-di(1,1-dimethylethyl)-4-hydroxyphenyl]-propionate, tris[2,4-di(1,1-dimethylethyl)-phenyl]-phosphite, 2,2'-di(octadecyloxy)-5,5'-spirobi(1,3,2-dioxaphosphorinane), dioctadecyl disulphide, didodecyl-3,3'-thiodipropionate, dioctadecyl-3,3'-thiodipropionate, butylhydroxytoluene, ethylene bis[3,3-di[3-(1,1-dimethylethyl)-4-hydroxyphenyl]butyrate] and mixtures thereof. The preferred oxidative stabilization agents are diethylenetriaminepentaacetic acid ("DTPA"), or salts of DTPA such as CaNa3DTPA, ZnNa3DTPA, and Ca2DTPA. See, U.S. App. Pat. No. 60/783,557 filed on, Mar. 17, 2006, entitled "Methods for Stabilizing Oxidatively Unstable Pharmaceutical Compositions" and its corresponding non-provisional filing which are hereby incorporated by reference in their entirety. In certain embodiments, the concentration of oxidative stabilization agents in the solution be from about 2.5 µmoles/liter to about, 5000 µmoles/liter, optionally, from about 20 µmoles/liter to about 1000 µmoles/liter, optionally from about 100 µmoles/liter to about 1000 µmoles/liter, or optionally from about 100 µmoles/liter to about 500 µmoles/liter.

In particular embodiments, the compositions of the present invention are formulated for administration at any frequency of administration, including once a week, once every five days, once every three days, once every two days, twice a day, three times a day, four times a day, five times a day, six times a day, eight times a day, every hour, or greater frequency. Such dosing frequency is also maintained for a varying duration of time depending on the therapeutic needs of the user. The duration of a particular therapeutic regimen may vary from one-time dosing to a regimen that extends for months or years. One of ordinary skill in the art would be familiar with determining a therapeutic regimen for a specific indication.

The composition and products containing such compositions of this invention may be prepared using methodology that is well known by an artisan of ordinary skill.

EXAMPLES

Any compositions of the present invention as described in following examples illustrate specific embodiments of compositions of the present invention, but are not intended to be limiting thereof. Other modifications can be undertaken by the skilled artisan without departing from the spirit and scope of this invention.

The following test methods were used in the Examples:

Example 1

To reduce obstruction potentially caused by tight junction structures (i.e., those surface structures [e.g., membrane or film barriers] typically inhibiting chemical permeation into tissues), induction of mucin secretion in human epicorneal 3D tissues was observed by contacting the corneal tissues with growth media containing *Pichia anomala* ferment extracts (Hyalurodine) (i.e., "treated" media) such that the bottom cell layer of the corneal tissues (i.e., cell layer which don't have tight junction structures inhibiting chemical permeation into tissues) were immersed in the growth media. By contacting the bottom cell layer of the corneal tissues with the growth media containing the *Pichia anomala* ferment extracts, the extract can directly contact and move upward into the inner corneal tissues without having to first pass through any tight junction structures or other surface barrier, providing improved bioavailability of *Pichia anomala* into corneal tissue cells.

Human epicorneal 3D tissues in growth media treated to have 1.56 mg/ml and 1.95 mg/ml concentrations of *Pichia anomala* ferment extracts (Hyalurodine) showed an increase of MUC4 gene expressions in the human epicorneal 3D tissues.

EpiCorneal 3D human tissues were purchased from Mat-Tek Company (Ashland, Mass., USA). Upon receiving the epicorneal 3D human tissues, they were incubated in Mat-Tek assay medium overnight following the manufacturer's instruction. The epicorneal 3D human tissues were divided into three treatment groups with three tissues per group. *Pichia anomala* ferment extracts (Hyalurodine) were added, respectively, into the culture medium containing the human epicorneal tissues of two of the treatment groups to produce media concentrations of 1.56 mg/ml and 1.95 mg/ml, respectively. The epicorneal tissues in all treatment groups were allowed to incubate for two days. The *Pichia anomala* ferment extract was supplied by Silab, St. Viance, France. After the two days, the human epicorneal 3D tissues were cut in halves and half of the tissues were lysed in 350 µL lysis buffer, consisting of 100 parts RLT buffer (RNeasy Mini kit, Qiagen, Valencia, Calif.), to one part 2-mercaptoethanol. RNA was extracted from the solutions using the RNeasy Mini Kit (Qiagen, Valencia, Calif.) according to manufacturer's instructions and RNA was eluted in 25 µL RNase-free water.

Reverse transcription (RT) was performed using the Applied Biosystems High Capacity Reverse Transcription Kit (ThermoFisher Scientific, Bridgewater, N.J.). Gene expression assays sold under the tradename TAQMAN for mucin-4 (MUC4), polymerase (RNA) II polypeptide A (POLR2A), and Master Mix were purchased from ThermoFisher Scientific (Bridgewater, N.J.). qPCR analysis was performed using TaqMan® Master Mix (ThermoFisher Scientific, Bridgewater, N.J.), and run on a real time PCR system sold under the tradename QUANTSTUDIO 7 Flex System (ThermoFisher Scientific, Bridgewater, N.J.). The expression of the MUC4 gene was normalized against the expression of the human POLR2A housekeeping gene. The fold changes were calculated in comparison to the untreated control (UT) and two-tailed two-sample Student t-tests (Microsoft Office Excel 2007; Microsoft, Redmond, Wash., USA) were performed. Results were shown in FIG. 1, indicating increased fold changes of MUC4 in corneal tissue cells with increased concentration of *Pichia anomala* ferment extract in media. The "untreated" sample was prepared the same as described this example except no *Pichia anomala* is added to media.

Example 2

Human epicorneal 3D tissues in growth media treated to contain 0.39 mg/ml, 0.78 mg/ml, 1.56 mg/ml and 1.95 mg/ml concentrations of *Pichia anomala* ferment extracts (Hyalurodine) showed an increase of MUC4 gene expressions in human epicorneal 3D tissues. *, p<0.05.

Figure 2:
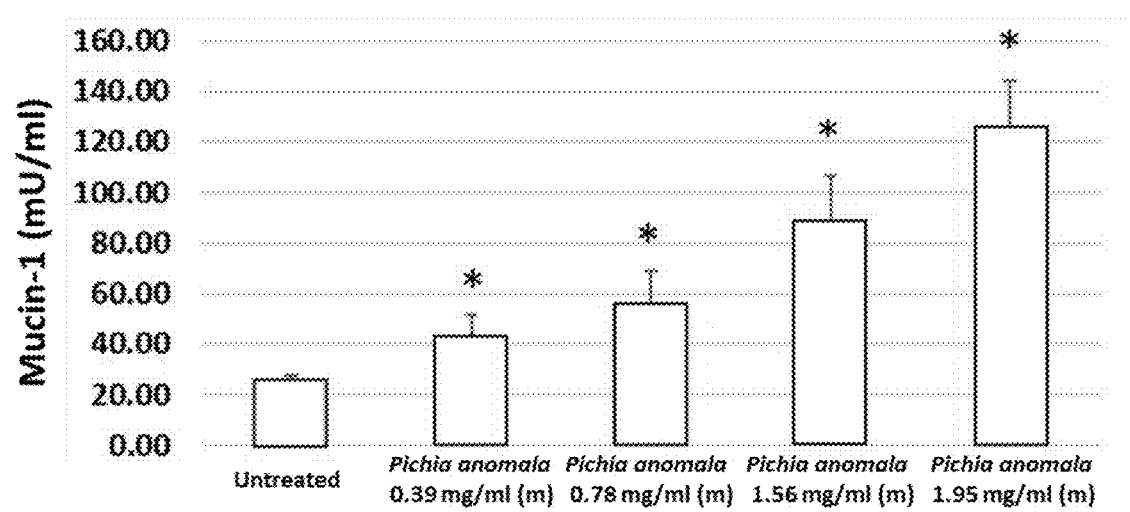
FIG. 2 depicts bar graphs showing increase in mucin-1 secretion in corneal epithelial cells after adding *Pichia anomala* extract to growth medium containing corneal epithelial cells.

EpiCorneal 3D human tissues were purchased from Mat-Tek Company (Ashland, Mass., USA). Upon receiving the epicorneal 3D human tissues, they were incubated in Mat-Tek assay medium overnight following the manufacturer's instruction. The epicorneal 3D human tissues were divided into five treatment groups with three tissues per group. *Pichia anomala* ferment extracts (Hyalurodine) were added, respectively, into the culture medium of four of the treatment groups to produce media concentrations of 0.39 mg/ml, 0.78 mg/ml, 1.56 mg/ml and 1.95 mg/ml, respectively. The epicorneal tissues of all five of the treatment groups allowed to incubate for two days. The *Pichia anomala* ferment extract was supplied by Silab, St. Viance, France. After the two days, culture media were collected for measuring mucin 1 secretion using human mucin-1 (CA15-3) enzyme-linked immunosorbent assay (ELISA) kit (EHMUC1, ThermoFisher Scientific, Bridgewater, N.J.) following the manufacturer's protocol. To assess activity, the colorimetric change was measured using a microplate reader (SpectraMax M2E, Molecular Devices, Sunnyvale, Calif., USA). This assay employs the standard enzyme-linked immunosorbent assay technique, so there is a linear correlation between Mucin-1 concentration in the sample and the colorimetric change. A standard curve was generated, with the Mucin-1 concentration on the x-axis and absorbance on the y-axis to indicate corresponding Mucin-1 concentration. Results were shown in FIG. 2, indicating increased Mucin-1 production in corneal tissue cells with increased environmental concentration of *Pichia anomala* ferment extract in media.

Example 3

Compositions having the 1.95 mg/ml, 7.8 mg/ml, 19.5 mg/ml and 39 mg/ml concentrations of *Pichia anomala* extracts in PBS showed an increase of mucin-1 secretion in human epicorneal 3D tissues when applied topically to corneal tissue cells. *, p<0.05.

Figure 3:
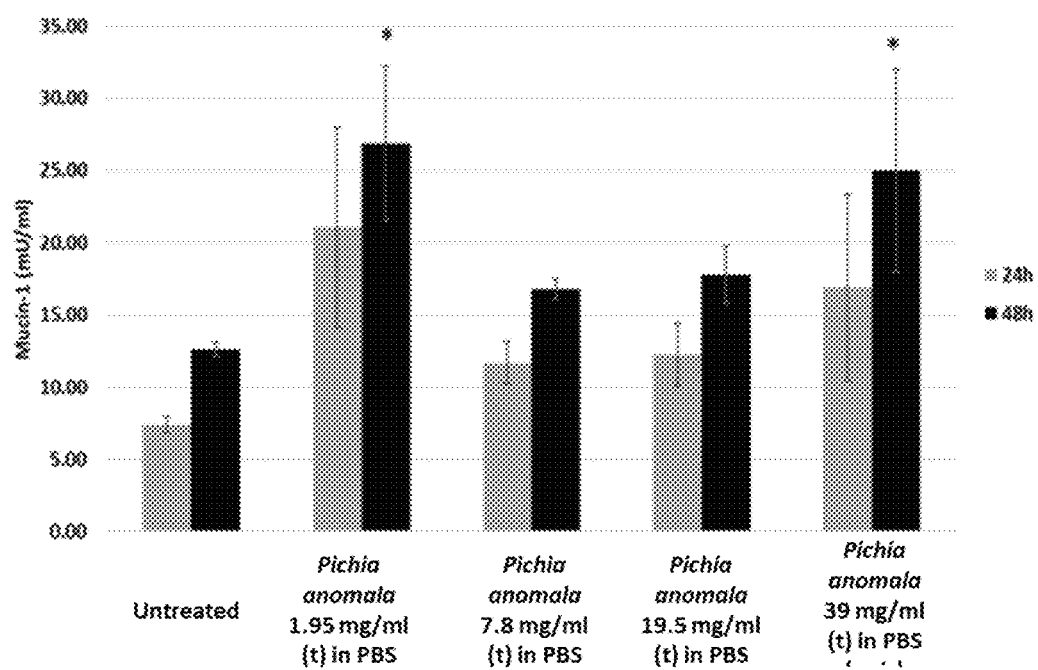
FIG. 3 depicts bar graphs showing increased Mucin-1 production in corneal tissue cells after topical applications of *Pichia anomala* extract.

EpiCorneal 3D human tissues were purchased from Mat-Tek Company (Ashland, Mass., USA). Upon receiving the epicorneal 3D human tissues, they were incubated in Mat-Tek assay medium overnight following the manufacturer's instruction. The epicorneal 3D human tissues were divided into three treatment groups with three tissues per group. Four concentrations of *Pichia anomala* ferment extracts (Hyalurodine) 1.95 mg/ml, 7.8 mg/ml, 19.5 mg/ml and 39 mg/ml were suspended in aqueous phosphate buffered solution (PBS) vehicles and were topically applied, respectively, to the corneal epithelium surface of four of the treatment groups. The epicorneal tissues of all five treatment groups were allowed to incubate for two days. The *Pichia anomala* ferment extract was supplied by Silab, St. Viance, France. After the two days, culture media were collected for measuring mucin 1 secretion using human mucin-1 (CA15-3) enzyme-linked immunosorbent assay (ELISA) kit (EHMUC1, ThermoFisher Scientific, Bridgewater, N.J.) following the manufacturer's protocol. To assess activity, the colorimetric change was measured using a microplate reader (SpectraMax M2E, Molecular Devices, Sunnyvale, Calif., USA). This assay employs the standard enzyme-linked immunosorbent assay technique, so there is a linear correlation between Mucin-1 concentration in the sample and the colorimetric change. A standard curve was generated, with the Mucin-1 concentration on the x-axis and absorbance on the y-axis to indicate corresponding Mucin-1 concentration. Results were shown in FIG. 3. (Kiwi is used in FIG. 2 to represent *Pichia anomala* ferment extract).

The results show that increased Mucin-1 production in corneal tissue cells was observed after topical application of compositions having the 1.95 mg/ml, 7.8 mg/ml, 19.5 mg/ml and 39 mg/ml concentrations of *Pichia anomala* extracts (in PBS).

Example 4

*Pichia anomala* ferment extracts (Hyalurodine) induced hyaluronic acid secretion in human epicorneal 3D tissues when applied topically to corneal tissue cells. Without being limited by theory, it is believed that such topical application requires diffusion of the *Pichia anomala* ferment extracts through tight junction structures of the human epicorneal tissue (i.e., those structures [e.g., membrane or film barriers] typically inhibiting chemical permeation into tissues) to reach the inside of the epicorneal tissue.

Figure 4:
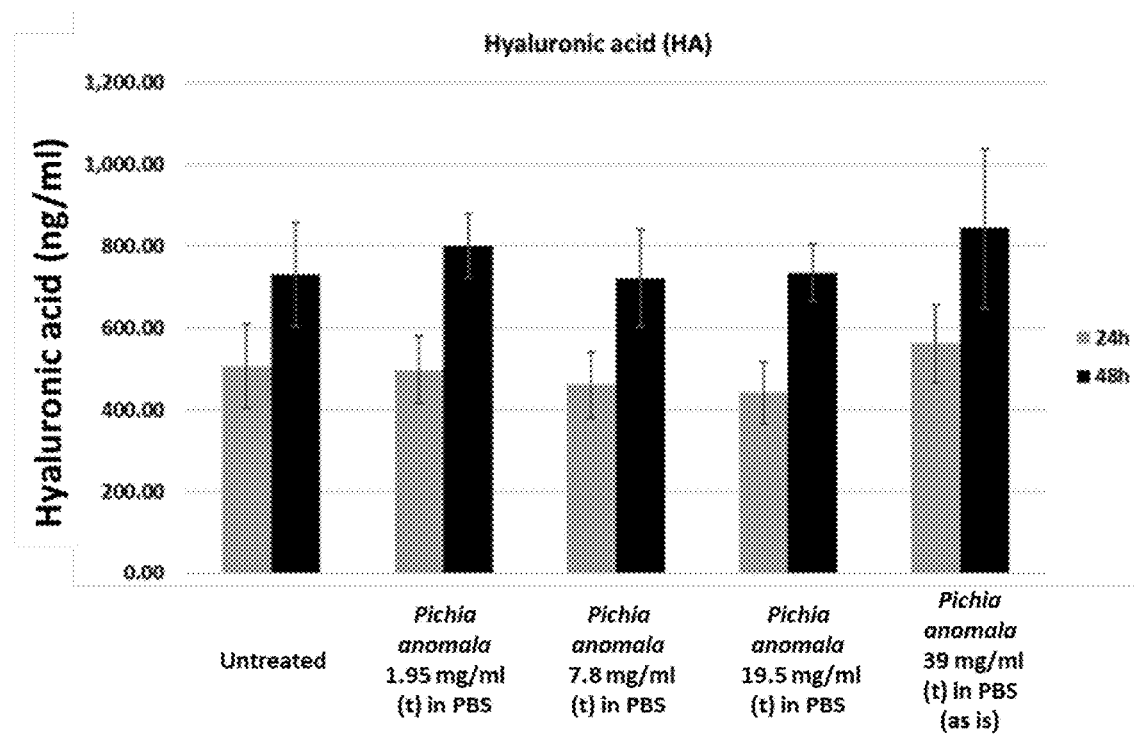
FIG. 4 depicts bar graphs showing increased HA production in corneal epithelial cells after topical applications of *Pichia anomala* extract at 24 and 48 hours.

EpiCorneal 3D human tissues were purchased from Mat-Tek Company (Ashland, Mass., USA). Upon receiving the epicorneal 3D human tissues, they were incubated in Mat-Tek assay medium overnight following the manufacturer's instruction. The epicorneal 3D human tissues were divided into five treatment groups with three tissues per group. Four concentrations of *Pichia anomala* ferment extracts (Hyalurodine) 1.95 mg/ml, 7.8 mg/ml, 19.5 mg/ml and 39 mg/ml in aqueous phosphate buffered solution (PBS) vehicle were topically applied, respectively, to the corneal epithelium surface of four of the treatment groups (such that the *Pichia anomala* ferment extracts were delivered through the above-mentioned tight junction structures). The epicorneal tissues in all five treatment groups were allowed to incubate for two days. The *Pichia anomala* ferment extract was supplied by Silab, St. Viance, France. After the two days, the culture media were collected for measuring hyaluronic acid (HA) secretion using HA enzyme-linked immunosorbent assay (ELISA) kit (K-1200, Echelon, Salt Lake City, Utah, USA) following the manufacturer's protocol. To assess activity, the colorimetric change was measured using a microplate reader (SpectraMax M2E, Molecular Devices, Sunnyvale, Calif., USA). This assay employs the competitive enzyme-linked immunosorbent assay technique, so there is an inverse correlation between HA concentration in the sample and the colorimetric change. A standard curve was generated, with the HA concentration on the x-axis and absorbance on the y-axis to indicate corresponding HA concentration. Results were shown in FIG. 4.

While the results suggest that topical application at the tested concentration directionally indicate induction of HA production in the corneal cells, factors such as tight junction structures (or, other surface membrane or film layer barriers) may reduce the concentration of *Pichia anomala* reaching the internal corneal tissues. In such situations, embodiments of the present invention incorporating penetration enhancers may be useful.

Example 5

To reduce obstruction potentially caused by the above tight junction structures (or, membrane or film barriers), induction of hyaluronic acid secretion in human epicorneal 3D tissues was observed by contacting the corneal tissues with growth media containing *Pichia anomala* ferment extracts (Hyalurodine) (i.e., "treated" media) such that the bottom cell layer of the corneal tissues (i.e., cell layers which don't have tight junction structures inhibiting chemical permeation into tissues) were immersed in the growth media. By contacting the bottom cell layer of the corneal tissues with the growth media containing the *Pichia anomala* ferment extracts, the extract can directly contact and move upward into the inner corneal tissues without having to first pass through any tight junction structures or other surface barrier, providing improved bioavailability of *Pichia anomala* into corneal tissue cells.

Figure 5:
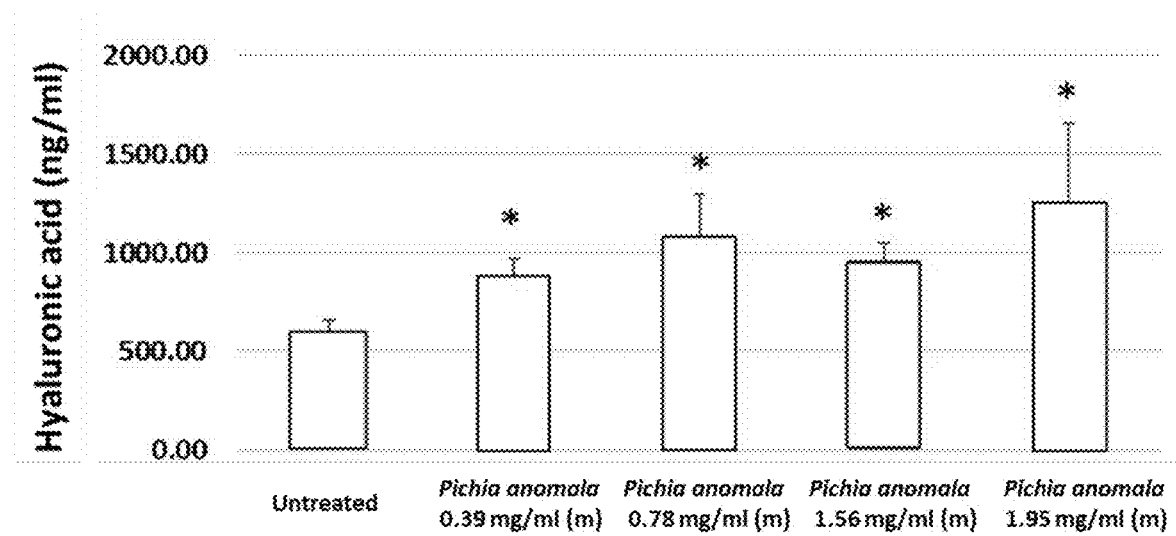
FIG. 5 depicts bar graphs showing statistically significant increase in HA production in corneal epithelial cells at 48 hours after placing corneal epithelial cells in growth medium containing *Pichia anomala* extract.

EpiCorneal 3D human tissues were purchased from Mat-Tek Company (Ashland, Mass., USA). Upon receiving the epicorneal 3D human tissues, these tissues were incubated in MatTek assay medium overnight following the manufacturer's instruction. The epicorneal 3D human tissues were divided into five treatment groups with three tissues per group. *Pichia anomala* ferment extracts (Hyalurodine) were added into the culture medium of four of the treatment groups to produce media concentrations of 0.39 mg/ml, 0.78 mg/ml, 1.56 mg/ml and 1.95 mg/ml, respectively, to contact the bottom cell layer of the human epicorneal tissues. The epicorneal tissues of all five of the treatment groups were allowed to incubate for two days. The *Pichia anomala* ferment extract was supplied by Silab, St. Viance, France. After the two days, the culture media were collected for measuring hyaluronic acid (HA) secretion using HA enzyme-linked immunosorbent assay (ELISA) kit (K-1200, Echelon, Salt Lake City, Utah, USA) following the manufacturer's protocol. To assess activity, the colorimetric change was measured using a microplate reader (SpectraMax M2E, Molecular Devices, Sunnyvale, Calif., USA). This assay employs the competitive enzyme-linked immunosorbent assay technique, so there is an inverse correlation between HA concentration in the sample and the colorimetric change. A standard curve was generated, with the HA concentration on the x-axis and absorbance on the y-axis to indicate corresponding HA concentration. Results were shown in FIG. 5.

The results show that a statistically significant increase in HA production in corneal tissue cells was observed at such tissue environmental concentrations of *Pichia anomala* of at least 0.3 mg/ml (i.e., concentrations of *Pichia anomala* extract contacting such internal corneal tissue cells [e.g., corneal fluid level concentrations]).

Example 6

Table 1 illustrates the components of such formulations (as shown in formulations 6A and 6B), which components can be incorporated as described below using conventional mixing technology.

TABLE 1

| INGREDIENT | 6A Useful for Relief of Dry Eye Irritation | | 6B Useful for Relief of Dry Eye Irritation for Contact Lenses | |
|---|---|---|---|---|
| | % w/w | amount per batch (gms) | % w/w | amount per batch (gms) |
| Sodium Hyaluronate | 0.20 | 2.0 | 0.15 | 1.5 |
| *Pichia anomala* extract | 2.0 | 20.0 | 5.0 | 50.0 |
| Polysorbate 80 | 1.0 | 10.0 | 2.0 | 20.0 |
| Polysorbate 20 | 5.0 | 50.0 | 10.0 | 100.0 |
| Polyethylene Glycol 400 | 0.25 | 2.5 | 0 | 0 |
| Boric Acid | 0.60 | 6.0 | 0.60 | 6.0 |
| Sodium Borate | 0.05 | 0.50 | 0.05 | 0.50 |
| Sodium Chloride* | | | | |
| Potassium Chloride | 0.10 | 1.0 | 0.10 | 1.0 |
| Calcium Chloride Dihydrate | 0.006 | 0.06 | 0.006 | 0.06 |
| Magnesium Chloride | 0.006 | 0.06 | 0.006 | 0.06 |
| Sodium Chlorite Dihydrate | 0.014 | 0.14 | 0.014 | 0.14 |
| Polyquaternium 42 (33% aqueous) | 0.0015 | 0.015 | 0.0015 | 0.015 |
| Sodium Chlorite Dihydrate | 0.014 | 0.14 | 0.014 | 0.14 |
| 1N Sodium Hydroxide solution** | | | | |
| 1N Hydrochloric Acid solution** | | | | |
| Purified Water*** | | | | |
| total | 100.00% | 1000.0 g | 100.00% | 1000.00 g |

*adjust to tonicity of 280-290 mOsm/Kg
**adjust to pH 7.2
***q.s to 100% w/w

For Examples 6A-6B: The Sodium Hyaluronate can be supplied by CONTIPRO A.S. (DOLNI, DOBROUC, CZECH REPUBLIC)
For Examples 6A and 6B: The *Pichia anomala* extract supplied by SILAB (SAINT VIANCE, FRANCE).
For Examples 6A-6B: The Polysorbate 20 can be supplied by Merck KGaA (DARMSTADT, GERMANY).
For Examples 6A-6B: The Polysorbate 80 can be supplied by Merck KGaA (DARMSTADT, GERMANY).
For Examples 6A: The Polyethylene Glycol 400 can be supplied by Clariant Produkte (BURGKIRCHEN, GERMANY).
For Examples 6A-6B: The Boric Acid can be supplied by Merck KGaA (DARMSTADT, GERMANY).
For Examples 6A-6B: The Sodium Borate can be supplied by Merck KGaA (DARMSTADT, GERMANY).
For Examples 6A-6B: The Sodium Chloride can be supplied by Caldic (DUSSELDORF, GERMANY).
For Examples 6A-6B: The Potassium Chloride can be supplied by Merck KGaA (DARMSTADT, GERMANY).
For Examples 6A-6B: The Calcium Chloride Dihydrate can be supplied by Merck KGaA (DARMSTADT, GERMANY).

For Examples 6A-6B: The Magnesium Chloride can be supplied by KGaA (DARMSTADT, GERMANY).
For Examples 6A-6B: The Polyquaternium-42 (33% aqueous) can be supplied by DSM BIOMEDICAL (BERKELEY, Calif., USA).
For Examples 6A-6B: The Sodium Chlorite Dihydrate can be supplied by Oxychem (WICHITA, Kans., USA)
For Examples 6A-6B: The 1N Sodium Hydroxide can be supplied by VWR (RADNER, Pa., USA).
For Examples 6A-6B: The 1N Hydrochloric acid can be supplied by VWR (RADNER, Pa., USA).
Solution 6A can be prepared as follows:
1. To a 1500 ml beaker is added 800 grams of Purified Water USP.
2. To the above is added 10 g of Polysorbate 80 and 50 g of Polysorbate 20. The solution is mixed until both are fully mixed and dissolved.
3. To the above is added 20.0 g of *Pichia anomala* extract. The solution is mixed until the *Pichia anomala* extract is dissolved.
4. The solution is filtered through a 0.45 micron filter and returned to a 1500 ml beaker.
5. To the solution of Step 4 is added 2.0 grams of Sodium Hyaluronate. The solution is mixed to fully dissolve the Sodium Hyaluronate.
6. The following ingredients are next added sequentially, allowing for each to dissolve before adding the next: 2.5 grams Polyethylene Glycol 400, 6.0 grams Boric acid, 0.05 gram Sodium Borate, 1.0 gram Potassium Chloride, 0.06 gram Calcium Chloride Dihydrate, 0.06 gram Magnesium Chloride, and 0.0015 grams Polyquaternium-42 (aqueous).
While continuing to mix, 0.14 gram Sodium Chlorite Dihydrate is added and mixed to dissolve.
8. The tonicity of the formula is determined and adjusted to 280 mOsm/Kg with Sodium Chloride.
9. The pH of the formula is adjusted to pH of 7.2 using the 1N Sodium Hydroxide and/or 1N Hydrochloric acid.
10. The solution is brought to 1000.0 grams using Purified Water USP and mixed for 10 minutes to be fully uniform.
11. The solution is filtered using a 0.22 micron filter.
Solution 6B can be prepared as follows:
1. To a 1500 ml beaker is added 800 grams of Purified Water USP.
2. To the above is added 20 g of Polysorbate 10 and 100 g of Polysorbate 20. The solution is mixed until both are fully mixed and dissolved.
3. To the above is added 50 g of *Pichia anomala* extract. The solution is mixed until the *Pichia anomala* extract is dissolved.
4. The solution is filtered through a 0.45 micron filter and returned to a 1500 ml beaker.
5. To the solution of Step 4 is added 1.5 grams of Sodium Hyaluronate. The solution is mixed to fully dissolve the Sodium Hyaluronate.
6. The following ingredients are next added sequentially, allowing for each to dissolve before adding the next: 6.0 grams Boric acid, 0.05 gram Sodium Borate, 1.0 gram Potassium Chloride, 0.06 gram Calcium Chloride Dihydrate, 0.06 gram Magnesium Chloride and 0.0015 grams Polyquaternium-42 (aqueous).
7. While continuing to mix, 0.14 gram Sodium Chlorite Dihydrate is added and mixed to dissolve.
8. The tonicity of the formula is determined and adjusted to 280 mOsm/Kg with Sodium Chloride.
9. The pH of the formula is adjusted to pH of 7.2 using the 1N Sodium Hydroxide and/or 1N Hydrochloric acid.
10. The solution is brought to 1000.0 grams using Purified Water USP and mixed for 10 minutes to be fully uniform.
11. The solution is filtered using a 0.22 micron filter.

Example 7

Table 2 illustrates the components of formulations of the present invention (as shown in formulations 7A and 7B), which components can be incorporated as described below using conventional mixing technology.

TABLE 2

| INGREDIENT | 7A Useful for Relief of Dry Eye Irritation | | 7B Useful for Relief of Dry Eye Irritation for Contact Lenses | |
|---|---|---|---|---|
| | % w/w | amount per batch (gms) | % w/w | amount per batch (gms) |
| *Pichia anomala* extract | 1.0 | 10.0 | 2.0 | 20.0 |
| Polysorbate 80 | 1.0 | 10.0 | 1.0 | 10.0 |
| Polysorbate 20 | 3.0 | 30.0 | 5.0 | 50.0 |
| Glycerin | 0.25 | 2.5 | 0.25 | 2.5 |
| Hypromellose E3 2910 | 0.198 | 1.98 | 0.198 | 1.98 |
| Boric Acid | 0.40 | 4.0 | 0.40 | 4.0 |
| Sodium Borate | 0.022 | 0.22 | 0.022 | 0.22 |
| Disodium Phosphate | 0.027 | 0.27 | 0.027 | 0.27 |
| Sodium Citrate Dihydrate | 0.40 | 4.0 | 0.40 | 4.0 |
| Sodium Chloride* | | | | |
| Potassium Chloride | 0.10 | 1.0 | 0.10 | 1.0 |
| 50% Aqueous Solution of Sodium Lactate | 0.057 | 0.57 | 0.057 | 0.57 |
| Magnesium Chloride | 0.013 | 0.13 | 0.013 | 0.13 |
| Glucose | 0.0036 | 0.036 | 0.0036 | 0.036 |
| Glycine | 0.00002 | 0.0002 | 0.00002 | 0.0002 |
| Ascorbic Acid | 0.00001 | 0.0001 | 0.00001 | 0.0001 |
| Disodium Edetate | 0.01 | 0.1 | 0.05 | 0.5 |
| Polyquaternium 42 (33% aqueous) | 0.0030 | 0.030 | 0.0015 | 0.015 |
| Sodium Chlorite Dihydrate | 0.014 | 0.14 | 0.014 | 0.14 |
| 1N Sodium Hydroxide solution** | | | | |
| 1N Hydrochloric Acid solution** | | | | |
| Purified Water*** | | | | |
| total | 100.00% | 1000.00 g | 100.00% | 1000.00 g |

*adjust to tonicity of 280-290 mOsm/Kg
**adjust to pH 7.2
***q.s to 100.00% volume For Examples 7A and 7B: The *Pichia anomala* extract can be supplied by SILAB (SAINT VIANCE, FRANCE).
For Examples 7A-7B: The Polysorbate 20 can be supplied by Merck KGaA (DARMSTADT, GERMANY).
For Examples 7A-7B: The Polysorbate 80 can be supplied by Merck KGaA (DARMSTADT, GERMANY).
For Examples 7A-7B The Boric Acid can be supplied by Merck KGaA (DARMSTADT, GERMANY).
For Examples 7A-7B: The Sodium Borate can be supplied by Merck KGaA (DARMSTADT, GERMANY).
For Examples 7A-7B: The Sodium Chloride can be supplied by Caldic (DUSSELDORF, GERMANY).
For Examples 7A-7B: The Potassium Chloride can be supplied by Merck KGaA (DARMSTADT, GERMANY).
For Examples 7A-7B: The Hypromellose E3 2910 can be supplied by DOW CHEMICAL (PLAQUEMINE, LOUISIANA, USA).

For Examples 7A-7B: The Glycerin can be supplied by Emery Oleochemicals GmbH (DUSSELDORF, GERMANY).

For Examples 7A-7B: The Disodium Phosphate can be supplied by Merck KGaA (DARMSTADT, GERMANY).

For Examples 7A-7B: The Sodium Citrate can be supplied by Merck KGaA (DARMSTADT, GERMANY).

For Examples 7A-7B: The Sodium Lactate can be supplied as Sodium Lactate (50% aqueous) by Merck KGaA (DARMSTADT, GERMANY).

For Examples 7A-7B: The Glucose can be supplied by Roquette Freres (LASTREM, FRANCE).

For Examples 7A-7B: The Glycine can be supplied by Merck KGaA (DARMSTADT, GERMANY).

For Examples 7A-7B: The Ascorbic Acid can be supplied by DSM NUTRITIONAL Products (DRAKEMYRE, SCOTLAND, UK).

For Examples 7A-7B: The Polyquaternium 42 to be supplied as Polyquaternium 42 (33% aqueous) by DSM BIOMEDICAL, (BERKELEY, Calif.).

For examples 7A-7B: The Disodium Edetate can be supplied by Merck NV/SA (OVERUSE, BELGIUM).

For Examples 7A-7B: The 1N Sodium Hydroxide can be supplied by VWR (RADNER, Pa., USA).

For Examples 7A-7B: The 1N Hydrochloric acid can be supplied by VWR (RADNER, Pa., USA).

For Examples 7A-7B: The Sodium Chlorite Dihydrate to be supplied by Oxychem (WICHITA, Kans., USA)

Solution 7A can be prepared as follows:

1. To a 1500 ml beaker is added 800 grams of Purified Water USP.
2. To the above is added 10 g of Polysorbate 80 and 30 g of Polysorbate 20. The solution is mixed until both are fully mixed and dissolved.
3. To the above is added 10.0 g of *Pichia anomala* extract. The solution is mixed until the *Pichia anomala* extract is dissolved.
4. The solution is filtered through a 0.45 micron filter and returned to a 1500 ml beaker.
5. To the above is added 1.98 g of Hypromellose E3 Premium. The solution is mixed until the Hypromellose E3 Premium dissolved.
6. The following ingredients are next added sequentially, allowing each to dissolve before adding the next: 2.50 grams Glycerin, 4.0 grams Boric acid, 0.22 gram Sodium Borate, 0.27 gram Disodium Phosphate, 4.00 grams Sodium Citrate Dihydrate, 1 gram Potassium Chloride, 0.57 gram Sodium Lactate (50% aqueous), 0.13 gram Magnesium Chloride, 0.036 gram Glucose, 0.0002 gram Glycine, 0.0001 gram Ascorbic acid, 0.10 gram Disodium Edetate, 0.030 gram Polyquaternium-42 (33% aqueous), and 0.14 gram Sodium Chlorite.
7. The tonicity of the solution is determined and adjusted to 280 mOsm with Sodium Chloride.
8. The pH of the solution is measured and adjusted to 7.2 with 1N Sodium Hydroxide and/or 1N Hydrochloric acid.
9. The solution is brought to a volume of 1,000.00 grams with Purified Water and mixed for 10 minutes.
10. The solution is filtered using a 0.22 micron filter.

Solution 7B can be prepared as follows:

1. To a 1500 ml beaker is added 800 grams of Purified Water USP.
2. To the above is added 10 g of Polysorbate 80 and 50 g of Polysorbate 20. The solution is mixed until both are fully mixed and dissolved.
3. To the above is added 20.0 g of *Pichia anomala* extract. The solution is mixed until the *Pichia anomala* extract is dissolved.
4. The solution is filtered through a 0.45 micron filter and returned to a 1500 ml beaker.
5. To the above is added 1.98 g of Hypromellose E3 Premium. The solution is mixed until the Hypromellose E3 Premium dissolved.
6. The following ingredients are next added sequentially, allowing each to dissolve before adding the next: 2.50 grams Glycerin, 4.0 grams Boric acid, 0.22 gram Sodium Borate, 0.27 gram Disodium Phosphate, 4.00 grams Sodium Citrate Dihydrate, 1 gram Potassium Chloride, 0.57 gram Sodium Lactate (50% aqueous), 0.13 gram Magnesium Chloride, 0.036 gram Glucose, 0.0002 gram Glycine, 0.0001 gram Ascorbic acid, 0.05 gram Disodium Edetate, 0.015 gram Polyquaternium-42 (33% aqueous), and 0.14 gram Sodium Chlorite.
7. The tonicity of the solution is determined and adjusted to 280 mOsm with Sodium Chloride.
8. The pH of the solution is measured and adjusted to 7.2 with 1N Sodium Hydroxide and/or 1N Hydrochloric acid.
9. The solution is brought to a volume of 1,000.00 grams with Purified Water and mixed for 10 minutes.
10. The solution is filtered using a 0.22 micron filter.

Example 8

Table 3 illustrates the components of such formulations (as shown in formulations 8A and 8B), which components can be incorporated as described below using conventional mixing technology.

TABLE 3

| INGREDIENT | 8A Useful for Relief of Dry Eye Irritation | | 8B Useful for Relief of Dry Eye Irritation for Contact Lenses | |
|---|---|---|---|---|
| | % w/w | amount per batch (gms) | % w/w | amount per batch (gms) |
| Sodium Hyaluronate | 0.20 | 2.0 | 0.15 | 1.5 |
| Kiwi Extract | 2.0 | 20.0 | 5.0 | 50.0 |
| Polysorbate 80 | 1.0 | 10.0 | 2.0 | 20.0 |
| Polysorbate 20 | 5.0 | 50.0 | 10.0 | 100.0 |
| Polyethylene Glycol 400 | 0.25 | 2.5 | 0 | 0 |
| Boric Acid | 0.60 | 6.0 | 0.60 | 6.0 |
| Sodium Borate | 0.05 | 0.50 | 0.05 | 0.50 |
| Sodium Chloride* | | | | |
| Potassium Chloride | 0.10 | 1.0 | 0.10 | 1.0 |
| Calcium Chloride Dihydrate | 0.006 | 0.06 | 0.006 | 0.06 |
| Magnesium Chloride | 0.006 | 0.06 | 0.006 | 0.06 |
| Sodium Chlorite Dihydrate | 0.014 | 0.14 | 0.014 | 0.14 |
| Polyquaternium 42 (33% aqueous) | 0.0015 | 0.015 | 0.0015 | 0.015 |
| Sodium Chlorite Dihydrate | 0.014 | 0.14 | 0.014 | 0.14 |
| 1N Sodium Hydroxide solution** | | | | |
| 1N Hydrochloric Acid solution** | | | | |
| Purified Water*** | | | | |
| total | 100.00% | 1000.0 g | 100.00% | 1000.00 g |

*adjust to tonicity of 280-290 mOsm/Kg
**adjust to pH 7.2
***q.s to 100% w/w

For Examples 8A-8B: The Sodium Hyaluronate can be supplied by CONTIPRO A.S. (DOLNI, DOBROUC, CZECH REPUBLIC)

For Examples 8A and 8B: The Kiwi Extract (*Pichia anomala* yeast extract) can be supplied by SILAB (SAINT VIANCE, FRANCE).

For Examples 8A-8B: The Polysorbate 20 can be supplied by Merck KGaA (DARMSTADT, GERMANY).

For Examples 8A-8B: The Polysorbate 80 can be supplied by Merck KGaA (DARMSTADT, GERMANY).

For Examples 8A: The Polyethylene Glycol 400 can be supplied by Clariant Produkte (BURGKIRCHEN, GERMANY).

For Examples 8A-8B: The Boric Acid can be supplied by Merck KGaA (DARMSTADT, GERMANY).

For Examples 8A-8B: The Sodium Borate can be supplied by Merck KGaA (DARMSTADT, GERMANY).

For Examples 8A-8B: The Sodium Chloride can be supplied by Caldic (DUSSELDORF, GERMANY).

For Examples 8A-8B: The Potassium Chloride can be supplied by Merck KGaA (DARMSTADT, GERMANY).

For Examples 8A-8B: The Calcium Chloride Dihydrate can be supplied by Merck KGaA (DARMSTADT, GERMANY).

For Examples 8A-8B: The Magnesium Chloride can be supplied by KGaA (DARMSTADT, GERMANY).

For Examples 8A-8B: The Polyquaternium-42 (33% aqueous) can be supplied by DSM BIOMEDICAL (BERKELEY, Calif., USA).

For Examples 8A-8B: The Sodium Chlorite Dihydrate can be supplied by Oxychem (WICHITA, Kans., USA)

For Examples 8A-8B: The 1N Sodium Hydroxide can be supplied by VWR (RADNER, Pa., USA).

For Examples 8A-8B: The 1N Hydrochloric acid can be supplied by VWR (RADNER, Pa., USA).

Solution 8A can be prepared as follows:
1. To a 1500 ml beaker is added 800 grams of Purified Water USP.
2. To the above is added 10 g of Polysorbate 80 and 50 g of Polysorbate 20. The solution is mixed until both are fully mixed and dissolved.
3. To the above is added 20.0 g of Kiwi Extract. The solution is mixed until the Kiwi Extract is dissolved.
4. The solution is filtered through a 0.45 micron filter and returned to a 1500 ml beaker.
5. To the solution of Step 4 is added 2.0 grams of Sodium Hyaluronate. The solution is mixed to fully dissolve the Sodium Hyaluronate.
6. The following ingredients are next added sequentially, allowing for each to dissolve before adding the next: 2.5 grams Polyethylene Glycol 400, 6.0 grams Boric acid, 0.05 gram Sodium Borate, 1.0 gram Potassium Chloride, 0.06 gram Calcium Chloride Dihydrate, 0.06 gram Magnesium Chloride, and 0.0015 grams Polyquaternium-42 (aqueous).
7. While continuing to mix, 0.14 gram Sodium Chlorite Dihydrate is added and mixed to dissolve.
8. The tonicity of the formula is determined and adjusted to 280 mOsm/Kg with Sodium Chloride.
9. The pH of the formula is adjusted to pH of 7.2 using the 1N Sodium Hydroxide and/or 1N Hydrochloric acid.
10. The solution is brought to 1000.0 grams using Purified Water USP and mixed for 10 minutes to be fully uniform.
11. The solution is filtered using a 0.22 micron filter.

Solution 8B can be prepared as follows:
1. To a 1500 ml beaker is added 800 grams of Purified Water USP.
2. To the above is added 20 g of Polysorbate 10 and 100 g of Polysorbate 20. The solution is mixed until both are fully mixed and dissolved.
3. To the above is added 50 g of Kiwi Extract. The solution is mixed until the Kiwi Extract is dissolved.
4. The solution is filtered through a 0.45 micron filter and returned to a 1500 ml beaker.
5. To the solution of Step 4 is added 1.5 grams of Sodium Hyaluronate. The solution is mixed to fully dissolve the Sodium Hyaluronate.
6. The following ingredients are next added sequentially, allowing for each to dissolve before adding the next: 6.0 grams Boric acid, 0.05 gram Sodium Borate, 1.0 gram Potassium Chloride, 0.06 gram Calcium Chloride Dihydrate, 0.06 gram Magnesium Chloride and 0.0015 grams Polyquaternium-42 (aqueous).
7. While continuing to mix, 0.14 gram Sodium Chlorite Dihydrate is added and mixed to dissolve.
8. The tonicity of the formula is determined and adjusted to 280 mOsm/Kg with Sodium Chloride.
9. The pH of the formula is adjusted to pH of 7.2 using the 1N Sodium Hydroxide and/or 1N Hydrochloric acid.
10. The solution is brought to 1000.0 grams using Purified Water USP and mixed for 10 minutes to be fully uniform.
11. The solution is filtered using a 0.22 micron filter.

Example 9

Table 4 illustrates the components of formulations of the present invention (as shown in formulations 9A and 9B), which components can be incorporated as described below using conventional mixing technology.

TABLE 4

| INGREDIENT | 9A Useful for Relief of Dry Eye Irritation | | 9B Useful for Relief of Dry Eye Irritation for Contact Lenses | |
|---|---|---|---|---|
| | % w/w | amount per batch (gms) | % w/w | amount per batch (gms) |
| Kiwi Extract | 1.0 | 10.0 | 2.0 | 20.0 |
| Polysorbate 80 | 1.0 | 10.0 | 1.0 | 10.0 |
| Polysorbate 20 | 3.0 | 30.0 | 5.0 | 50.0 |
| Glycerin | 0.25 | 2.5 | 0.25 | 2.5 |
| Hypromellose E3 2910 | 0.198 | 1.98 | 0.198 | 1.98 |
| Boric Acid | 0.40 | 4.0 | 0.40 | 4.0 |
| Sodium Borate | 0.022 | 0.22 | 0.022 | 0.22 |
| Disodium Phosphate | 0.027 | 0.27 | 0.027 | 0.27 |
| Sodium Citrate Dihydrate | 0.40 | 4.0 | 0.40 | 4.0 |
| Sodium Chloride* | | | | |
| Potassium Chloride | 0.10 | 1.0 | 0.10 | 1.0 |
| 50% Aqueous Solution of Sodium Lactate | 0.057 | 0.57 | 0.057 | 0.57 |
| Magnesium Chloride | 0.013 | 0.13 | 0.013 | 0.13 |
| Glucose | 0.0036 | 0.036 | 0.0036 | 0.036 |
| Glycine | 0.00002 | 0.0002 | 0.00002 | 0.0002 |
| Ascorbic Acid | 0.00001 | 0.0001 | 0.00001 | 0.0001 |

TABLE 4-continued

| | 9A Useful for Relief of Dry Eye Irritation | | 9B Useful for Relief of Dry Eye Irritation for Contact Lenses | |
|---|---|---|---|---|
| INGREDIENT | % w/w | amount per batch (gms) | % w/w | amount per batch (gms) |
| Disodium Edetate | 0.01 | 0.1 | 0.05 | 0.5 |
| Polyquaternium 42 (33% aqueous) | 0.0030 | 0.030 | 0.0015 | 0.015 |
| Sodium Chlorite Dihydrate | 0.014 | 0.14 | 0.014 | 0.14 |
| 1N Sodium Hydroxide solution** | | | | |
| 1N Hydrochloric Acid solution** | | | | |
| Purified Water*** | | | | |
| total | 100.00% | 1000.00 g | 100.00% | 1000.00 g |

*adjust to tonicity of 280-290 mOsm/Kg
**adjust to pH 7.2
***q.s to 100.00% volume For Examples 9A and 9B: The Kiwi Extract (*Pichia anomala* yeast extract) can be supplied by SILAB (SAINT VIANCE, FRANCE).
For Examples 9A-9B: The Polysorbate 20 can be supplied by Merck KGaA (DARMSTADT, GERMANY).
For Examples 9A-9B: The Polysorbate 80 can be supplied by Merck KGaA (DARMSTADT, GERMANY).
For Examples 9A-9B The Boric Acid can be supplied by Merck KGaA (DARMSTADT, GERMANY).
For Examples 9A-9B: The Sodium Borate can be supplied by Merck KGaA (DARMSTADT, GERMANY).
For Examples 9A-9B: The Sodium Chloride can be supplied by Caldic (DUSSELDORF, GERMANY).
For Examples 9A-9B: The Potassium Chloride can be supplied by Merck KGaA (DARMSTADT, GERMANY).
For Examples 9A-9B: The Hypromellose E3 2910 can be supplied by DOW CHEMICAL (PLAQUEMINE, LOUISIANA, USA).
For Examples 9A-9B: The Glycerin can be supplied by Emery Oleochemicals GmbH (DUSSELDORF, GERMANY).
For Examples 9A-9B: The Disodium Phosphate can be supplied by Merck KGaA (DARMSTADT, GERMANY).
For Examples 9A-9B: The Sodium Citrate can be supplied by Merck KGaA (DARMSTADT, GERMANY).
For Examples 9A-9B: The Sodium Lactate can be supplied as Sodium Lactate (50% aqueous) by Merck KGaA (DARMSTADT, GERMANY).
For Examples 9A-9B: The Glucose can be supplied by Roquette Freres (LASTREM, FRANCE).
For Examples 9A-9B: The Glycine can be supplied by Merck KGaA (DARMSTADT, GERMANY).
For Examples 9A-9B: The Ascorbic Acid can be supplied by DSM NUTRITIONAL Products (DRAKEMYRE, SCOTLAND, UK).
For Examples 9A-9B: The Polyquaternium 42 to be supplied as Polyquaternium 42 (33% aqueous) by DSM BIOMEDICAL, (BERKELEY, Calif.).
For examples 9A-9B: The Disodium Edetate can be supplied by Merck NV/SA (OVERUSE, BELGIUM).
For Examples 9A-9B: The 1N Sodium Hydroxide can be supplied by VWR (RADNER, Pa., USA).
For Examples 9A-9B: The 1N Hydrochloric acid can be supplied by VWR (RADNER, Pa., USA).
For Examples 9A-9B: The Sodium Chlorite Dihydrate to be supplied by Oxychem (WICHITA, Kans., USA)

Solution 9A can be prepared as follows:
1. To a 1500 ml beaker is added 800 grams of Purified Water USP.
2. To the above is added 10 g of Polysorbate 80 and 30 g of Polysorbate 20. The solution is mixed until both are fully mixed and dissolved.
3. To the above is added 10.0 g of Kiwi Extract. The solution is mixed until the Kiwi Extract is dissolved.
4. The solution is filtered through a 0.45 micron filter and returned to a 1500 ml beaker.
5. To the above is added 1.98 g of Hypromellose E3 Premium. The solution is mixed until the Hypromellose E3 Premium dissolved.
6. The following ingredients are next added sequentially, allowing each to dissolve before adding the next: 2.50 grams Glycerin, 4.0 grams Boric acid, 0.22 gram Sodium Borate, 0.27 gram Disodium Phosphate, 4.00 grams Sodium Citrate Dihydrate, 1 gram Potassium Chloride, 0.57 gram Sodium Lactate (50% aqueous), 0.13 gram Magnesium Chloride, 0.036 gram Glucose, 0.0002 gram Glycine, 0.0001 gram Ascorbic acid, 0.10 gram Disodium Edetate, 0.030 gram Polyquaternium-42 (33% aqueous), and 0.14 gram Sodium Chlorite.
7. The tonicity of the solution is determined and adjusted to 280 mOsm with Sodium Chloride.
8. The pH of the solution is measured and adjusted to 7.2 with 1N Sodium Hydroxide and/or 1N Hydrochloric acid.
9. The solution is brought to a volume of 1,000.00 grams with Purified Water and mixed for 10 minutes.
10. The solution is filtered using a 0.22 micron filter.

Solution 9B can be prepared as follows:
1. To a 1500 ml beaker is added 800 grams of Purified Water USP.
2. To the above is added 10 g of Polysorbate 80 and 50 g of Polysorbate 20. The solution is mixed until both are fully mixed and dissolved.
3. To the above is added 20.0 g of Kiwi Extract. The solution is mixed until the Kiwi Extract is dissolved.
4. The solution is filtered through a 0.45 micron filter and returned to a 1500 ml beaker.
5. To the above is added 1.98 g of Hypromellose E3 Premium. The solution is mixed until the Hypromellose E3 Premium dissolved.
6. The following ingredients are next added sequentially, allowing each to dissolve before adding the next: 2.50 grams Glycerin, 4.0 grams Boric acid, 0.22 gram Sodium Borate, 0.27 gram Disodium Phosphate, 4.00 grams Sodium Citrate Dihydrate, 1 gram Potassium Chloride, 0.57 gram Sodium Lactate (50% aqueous), 0.13 gram Magnesium Chloride, 0.036 gram Glucose, 0.0002 gram Glycine, 0.0001 gram Ascorbic acid, 0.05 gram Disodium Edetate, 0.015 gram Polyquaternium-42 (33% aqueous), and 0.14 gram Sodium Chlorite.
7. The tonicity of the solution is determined and adjusted to 280 mOsm with Sodium Chloride.
8. The pH of the solution is measured and adjusted to 7.2 with 1N Sodium Hydroxide and/or 1N Hydrochloric acid.
9. The solution is brought to a volume of 1,000.00 grams with Purified Water and mixed for 10 minutes.
10. The solution is filtered using a 0.22 micron filter.

EMBODIMENTS OF THE PRESENT INVENTION

1. A microemulsion composition or microemulsion for treating the eye comprising:
   i) one or more extracts, or sources of extracts, of the genus *Pichia*; and
   ii) an ophthalmologically acceptable carrier
   wherein the microemulsion droplets or particles have a maximum dimension of less than 1,500 Å.
2. The composition of embodiment 1 (or, any of the following embodiments), wherein the genus of *Pichia* is selected from *Pichia anomala, Pichia guilhermonchi, Pichia norvegensis, Pichia ohmeri* and mixtures thereof
3. The composition of embodiments 1and/or 2 (or, any of the following embodiments), wherein the genus of *Pichia* is *Pichia anomala*.
4. The composition of any one of or combination of embodiments 1 to 3 (or, any of the following embodiments), where in the one or more extracts, or sources of extracts, of the genus *Pichia* are present at a concentration of from about 0.01% to about 100% by weight of the total composition.
5. The composition of any one of or combination of embodiments 1 to 4 (or, any of the following embodiments), where in the one or more extracts, or sources of extracts, of the genus *Pichia* are present at a concentration of from about 0.05% to about 95% by weight of the total composition.
6. The composition of any one of or combination of embodiments 1 to 5 (or, any of the following embodiments), where in the one or more extracts, or sources of extracts, of the genus *Pichia* are present at a concentration of from about 0.1% to about 90% by weight of the total composition.
7. The composition of any one of or combination of embodiments 1 to 6 (or, any of the following embodiments), comprising a permeation enhancer.
8. The composition of any one of or combination of embodiments 1 to 7 (or, any of the following embodiments), wherein the permeation enhancer is present at a concentration of from about 0.01% to about 20% (w/v) of the total composition.
9. The composition of any one of or combination of embodiments 1 to 8 (or, any of the following embodiments), wherein the permeation enhancer is present at a concentration of from about 0.1% to 10% (w/v) of the total composition.
10. The composition of any one of or combination of embodiments 1 to 9 (or, any of the following embodiments), wherein the permeation enhancer is present at a concentration of from about 0.25% to 5% (w/v) of the total composition,
11. The composition of any one of or combination of embodiments 1 to 10 (or, any of the following embodiments), wherein the permeation enhancer is selected from polyoxyethylene, polyoxyethylene ethers of fatty acids, sorbitan monooleate, sorbitan monolaurate, polyoxyethylene monolaurate, polyoxyethylene sorbitan monolaurate, fusidic acid and derivatives thereof, EDTA, disodium EDTA, cholic acid, deoxycholic acid, glycocholic acid, glycodeoxycholic acid, taurocholic acid, taurodeoxycholic acid, sodium cholate, sodium glycocholate, glycocholate, sodium deoxycholate, sodium taurocholate, sodium glycodeoxycholate, sodium taurodeoxycholate, chenodeoxycholic acid, urosdeoxycholic acid, saponins, glycyrrhizic acid, ammonium glycyrrhizide, decamethonium, decamethonium bromide, and dodecyltrimethylammonium bromide or mixtures of any of the above.
12. The composition of any one of or combination of embodiments 1 to 11 (or, any of the following embodiments), wherein the *Pichia* genus extract comprises oligosaccharides and polysaccharide having a weight average molecular weight of from about 180 to about 800,000 Da.
13. The composition of any one of or combination of embodiments 1 to 12 (or, any of the following embodiments), wherein the *Pichia* genus extract comprises oligosaccharides and polysaccharide having an average degree of polymerization of from DP 1 to DP 4444.
14. A method for producing/releasing/delivering/excreting mucin from and/or in the cornea comprising the step of administering a microemulsion composition comprising:
    i) one or more extracts, or sources of extracts, of the genus *Pichia*; and
    ii) optionally, an ophthalmologically acceptable carrier
    wherein the microemulsion droplets or particles have a maximum dimension of less than 1,500 Å.
15. The method according to embodiment 14 (or, any of the following embodiments), wherein the genus of *Pichia* is selected from *Pichia anomala, Pichia guilliermondil, Pichia norvegensis, Pichia ohmeri* and mixtures thereof
16. The method according to embodiments 14 and/or 15 (or, any of the following embodiments), wherein the genus of *Pichia* is *Pichia anomala*.
17. A method for maintaining the concentration of MU5AC in tears within the range of equal to or greater than 8 nanograms to 15 nanograms per milligrams of protein, comprising the step of administering a microemulsion composition comprising:
    i) one or more extracts, or sources of extracts, of the genus *Pichia*; and
    ii) optionally, an ophthalmologically acceptable carrier
    wherein the microemulsion droplets or particles have a maximum dimension of less than 1,500 Å.
18. A method for treating a patient having decreased or low-level production/release/delivery/excretion of mucin from and/or in the cornea comprising the step of topically administering to the eye the patient a microemultion composition comprising:
    i) one or more extracts, or sources of extracts, of the genus *Pichia*; and
    ii) optionally, an ophthalmologically acceptable carrier
    wherein the microemulsion droplets or particles have a maximum dimension of less than 1,500 Å.
19. A method for promoting healing or increasing the rate of healing of wounds in and/or on the eye of a patient, comprising the step of administering a microemulsion composition comprising:
    i) one or more extracts, or sources of extracts, of the genus *Pichia*; and
    ii) optionally, an ophthalmologically acceptable carrier
    wherein the microemulsion droplets or particles have a maximum dimension of less than 1,500 Å.
20. A method for improving the antimicrobial properties in tears of a patient, comprising the step of administering a microemulsion composition comprising:
    i) one or more extracts, or sources of extracts, of the genus *Pichia*; and
    ii) optionally, an ophthalmologically acceptable carrier
    wherein the microemulsion droplets or particles have a maximum dimension of less than 1,500 Å.

21. A method for treating a patient having decreased or low-level production/release/delivery/excretion of hyaluronic acid from and/or in the cornea comprising the step of topically administering to the eye of the patient a microemulsion composition comprising:
   i) a safe and effective amount of one or more extracts, or sources of extracts, of the genus *Pichia* to achieve a *Pichia* genus extract concentration in the corneal fluid in the corneal tissues of the eye of at least about 0.3 mg/ml;
   ii) optionally, a safe and effective amount of a permeation enhancer; and
   iii) optionally, an ophthalmologically acceptable carrier
   wherein the microemulsion droplets or particles have a maximum dimension of less than 1,500 Å.
22. The method of embodiment 21 (or, any of the following embodiments), wherein the *Pichia* genus extract in the composition comprises oligosaccharides and polysaccharide having a weight average molecular weight of from about 180 to about 800,000 Da.
23. The method of embodiment 21 and/or 22 (or, any of the following embodiments), wherein the *Pichia* genus extract in the composition comprises oligosaccharides and polysaccharide having an average degree of polymerization of from DP 1 to DP 4444.
24. The method of any one of or combination of embodiments 21 to 23 (or, any of the following embodiments), wherein the composition comprises a permeation enhancer.
25. The method of any one of or combination of embodiments 21 to 24 (or, any of the following embodiments), wherein the permeation enhancer is present at a concentration of from about 0.01% to about 20% (w/v) of the total composition.
26. The method of any one of or combination of embodiments 21 to 25 (or, any of the following embodiments), wherein the permeation enhancer is present at a concentration of from about 0.1% to 10% (w/v) of the total composition.
27. The method of any one of or combination of embodiments 21 to 26 (or, any of the following embodiments), wherein the permeation enhancer is present at a concentration of from about 0.25% to 5% (w/v) of the total composition,
28. The method of any one of or combination of embodiments 21 to 27 (or, any of the following embodiments), wherein the permeation enhancer is selected from polyoxyethylene, polyoxyethylene ethers of fatty acids, sorbitan monooleate, sorbitan monolaurate, polyoxyethylene monolaurate, polyoxyethylene sorbitan monolaurate, fusidic acid and derivatives thereof, EDTA, disodium EDTA, cholic acid, deoxycholic acid, glycocholic acid, glycodeoxycholic acid, taurocholic acid, taurodeoxycholic acid, sodium cholate, sodium glycocholate, glycocholate, sodium deoxycholate, sodium taurocholate, sodium glycodeoxycholate, sodium taurodeoxycholate, chenodeoxycholic acid, urosdeoxycholic acid, saponins, glycyrrhizic acid, ammonium glycyrrhizide, decamethonium, decamethonium bromide, and dodecyltrimethylammonium bromide or mixtures of any of the above.
29. The method of any one of or combination of embodiments 21 to 28 (or, any of the following embodiments), wherein the composition is administered when the hyaluronic acid concentration, in the patient's tears, is lower than about 10 nanograms per milligram of proteins.
30. The method of any one of or combination of embodiments 21 to 29 (or, any of the following embodiments), wherein the composition is administered when the hyaluronic acid concentration, in the patient's tears, is lower than about 15 nanograms per milligram of proteins.
31. The method of any one of or combination of embodiments 21 to 30 (or, any of the following embodiments), wherein the composition is administered when the hyaluronic acid concentration, in the patient's tears, is lower than about 20 nanograms per milligram of proteins.
32. The method of any one of or combination of embodiments 21 to 31 (or, any of the following embodiments), wherein the composition is administered when the hyaluronic acid concentration, in the patient's tears, is lower than about 25 nanograms per milligram of proteins.
33. The method of any one of or combination of embodiments 21 to 32 (or, any of the following embodiments), wherein the composition is administered to the patient's eye to raise the concentration of hyaluronic acid in the patient's tears to be equal to or greater than about 10 nanograms per milligram of proteins.
34. The method of any one of or combination of embodiments 21 to 33 (or, any of the following embodiments), wherein the composition is administered to the patient's eye to raise the concentration of hyaluronic acid in the patient's tears to be equal to or greater than about 15 nanograms per milligram of proteins.
35. The method of any one of or combination of embodiments 21 to 34 (or, any of the following embodiments), wherein the composition is administered to the patient's eye to raise the concentration of hyaluronic acid in the patient's tears to be equal to or greater than about 20 nanograms per milligram of proteins.
36. The method of any one of or combination of embodiments 21 to 35 (or, any of the following embodiments), wherein the composition is administered to the patient's eye to raise the concentration of hyaluronic acid in the patient's tears to be equal to or greater than about 25 nanograms per milligram of proteins.

What is claimed is:
1. A microemulsion composition for treating the eye comprising:
   i) one or more extracts, of the genus *Pichia*; and
   ii) an ophthalmologically acceptable carrier wherein the microemulsion droplets or particles have a maximum dimension of less than 1,500 Å.
2. The composition according to claim 1, wherein the genus of *Pichia* is selected from *Pichia anomala, Pichia guilliermondii, Pichia norvegensis, Pichia ohmeri* and mixtures thereof.
3. The composition according to claim 2, wherein the genus of *Pichia* is *Pichia anomala*.
4. The composition of claim 1, where in the one or more extracts, of the genus *Pichia* are present at a concentration of from about 0.001% to about 99% by weight of the total composition.
5. The composition of claim 1, where in the one or more extracts, or sources of extracts, of the genus *Pichia* are present at a concentration of from about 0.005% to about 95% by weight of the total composition.

6. The composition of claim 1, where in the one or more extracts, of the genus *Pichia* are present at a concentration of from about 0.01% to about 90% by weight of the total composition.

7. The composition according to claim 1, comprising a permeation enhancer.

8. The composition of claim 7 wherein the permeation enhancer is present at a concentration of from about 0.01% to about 20% (w/v) of the total composition.

9. The composition of claim 8 wherein the permeation enhancer is present at a concentration of from about 0.1% to 10% (w/v) of the total composition.

10. The composition of claim 9 wherein the permeation enhancer is present at a concentration of from about 0.25% to 5% (w/v) of the total composition.

11. The composition of claim 7 wherein the permeation enhancer is selected from polyoxyethylene, polyoxyethylene ethers of fatty acids, sorbitan monooleate, sorbitan monolaurate, polyoxyethylene monolaurate, polyoxyethylene sorbitan monolaurate, fusidic acid and derivatives thereof, EDTA, disodium EDTA, cholic acid, deoxycholic acid, glycocholic acid, glycodeoxycholic acid, taurocholic acid, taurodeoxycholic acid, sodium cholate, sodium glycocholate, glycocholate, sodium deoxycholate, sodium taurocholate, sodium glycodeoxycholate, sodium taurodeoxycholate, chenodeoxycholic acid, urosdeoxycholic acid, saponins, glycyrrhizic acid, ammonium glycyrrhizide, decamethonium, decamethonium bromide, and dodecyltrimethylammonium bromide or mixtures of any of the above.

12. The composition of claim 1 wherein the *Pichia* genus extract comprises oligosaccharides and polysaccharide having a weight average molecular weight of from about 180 to about 800,000 Da.

13. The composition of claim 1 wherein the *Pichia* genus extract comprises oligosaccharides and polysaccharide having an average degree of polymerization of from DP 1 to DP 4444.

* * * * *